(12) United States Patent
Souter et al.

(10) Patent No.: US 7,786,067 B2
(45) Date of Patent: Aug. 31, 2010

(54) COMPOSITION COMPRISING A LIPASE AND A BLEACH CATALYST

(75) Inventors: Philip Frank Souter, Northumberland (GB); Neil Joseph Lant, Newcastle upon Tyne (GB); Alan Thomas Brooker, Newcastle upon Tyne (GB); Gregory Scot Miracle, Hamilton, OH (US); Nicola Jane Binney, Newcastle upon Tyne (GB); David Lee Daugherty, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 668 days.

(21) Appl. No.: 11/656,265

(22) Filed: Jan. 22, 2007

(65) Prior Publication Data

US 2007/0173430 A1    Jul. 26, 2007

Related U.S. Application Data

(60) Provisional application No. 60/761,115, filed on Jan. 23, 2006, provisional application No. 60/796,324, filed on Apr. 28, 2006, provisional application No. 60/854,835, filed on Oct. 27, 2006.

(51) Int. Cl.
*C11D 17/00* (2006.01)
*C12N 9/20* (2006.01)

(52) U.S. Cl. ........................................ 510/419; 435/198
(58) Field of Classification Search ................ 510/226, 510/419; 435/198
See application file for complete search history.

(56) References Cited

U.S. PATENT DOCUMENTS

| | | |
|---|---|---|
| 4,678,792 A | 7/1987 | Nickl et al. |
| 5,045,223 A | 9/1991 | Batal et al. |
| 5,047,163 A | 9/1991 | Batal et al. |
| 5,360,568 A | 11/1994 | Madison et al. |
| 5,360,569 A | 11/1994 | Madison et al. |
| 5,370,826 A | 12/1994 | Madison et al. |
| 5,442,066 A | 8/1995 | Madison et al. |
| 5,478,357 A | 12/1995 | Madison et al. |
| 5,482,515 A | 1/1996 | Madison et al. |
| 5,550,256 A | 8/1996 | Madison et al. |
| 5,576,282 A | 11/1996 | Miracle et al. |
| 5,653,910 A | 8/1997 | Kerschner et al. |
| 5,710,116 A | 1/1998 | Miracle et al. |
| 5,753,599 A | 5/1998 | Coope et al. |
| 5,760,222 A | 6/1998 | Coope |
| 5,785,886 A | 7/1998 | Kerschner et al. |
| 5,817,614 A | 10/1998 | Miracle et al. |
| 5,869,438 A | 2/1999 | Svendsen et al. |
| 5,902,781 A | 5/1999 | Painter |
| 5,952,282 A | 9/1999 | Loffler et al. |
| 6,042,744 A | 3/2000 | Nation et al. |
| 6,649,085 B2 | 11/2003 | Reinhardt et al. |
| 6,939,702 B1 | 9/2005 | Vind et al. |
| 7,172,997 B2 * | 2/2007 | Minning et al. .............. 510/226 |
| 2007/0173429 A1 | 7/2007 | Souter et al. |
| 2007/0179074 A1 | 8/2007 | Souter et al. |
| 2007/0179075 A1 | 8/2007 | Souter et al. |
| 2007/0191247 A1 | 8/2007 | Souter et al. |
| 2007/0191248 A1 | 8/2007 | Souter et al. |
| 2007/0191249 A1 | 8/2007 | Lant et al. |
| 2007/0191250 A1 | 8/2007 | Lant et al. |

FOREIGN PATENT DOCUMENTS

| | | |
|---|---|---|
| EP | 0 728 181 B1 | 8/1996 |
| EP | 0 728 182 B1 | 8/1996 |
| EP | 0 728 183 B1 | 8/1996 |
| EP | 0 775 192 B1 | 5/1997 |
| EP | 0 851 913 B1 | 7/1998 |
| EP | 1 726 636 A1 | 11/2006 |
| WO | WO 92/05249 A1 | 4/1992 |
| WO | WO 94/07984 A1 | 4/1994 |
| WO | WO 94/25577 A1 | 11/1994 |
| WO | WO 95/00625 A1 | 1/1995 |
| WO | WO 95/13351 A1 | 5/1995 |
| WO | WO 95/13353 A1 | 5/1995 |
| WO | WO 95/22615 A1 | 8/1995 |
| WO | WO 97/04078 A1 | 2/1997 |
| WO | WO 97/04079 A1 | 2/1997 |
| WO | WO 97/07202 A1 | 2/1997 |
| WO | WO 97/10323 A1 | 3/1997 |
| WO | WO 98/16614 A1 | 4/1998 |
| WO | WO 98/17767 A1 | 4/1998 |

(Continued)

OTHER PUBLICATIONS

Cavicchioli, M. et al., "Oxyfunctionalization Reactions by Perfluora Cis-2, 3-dialkyloxaziridines. Enantioselective Conversion of Silanes Into Silanols," Tetrahedron Letters, vol. 35, No. 34, 1994, pp. 6329-6330.

(Continued)

*Primary Examiner*—Tekchand Saidha
(74) *Attorney, Agent, or Firm*—James F. McBride; Leonard W. Lewis; Steven W. Miller

(57) ABSTRACT

The present invention relates to a composition comprising: (i) a lipase; and (ii) a bleach catalyst that is capable of accepting an oxygen atom from a peroxyacid and transferring the oxygen atom to an oxidizeable substrate.

39 Claims, 3 Drawing Sheets

FOREIGN PATENT DOCUMENTS

| | | |
|---|---|---|
| WO | WO 99/42566 A1 | 8/1999 |
| WO | WO 00/42151 A1 | 7/2000 |
| WO | WO 00/42156 A1 | 7/2000 |
| WO | WO 00/60063 A1 | 10/2000 |
| WO | WO 01/16110 A1 | 3/2001 |
| WO | WO 01/16263 A2 | 3/2001 |
| WO | WO 01/16273 A1 | 3/2001 |
| WO | WO 01/16274 A1 | 3/2001 |
| WO | WO 01/16275 A1 | 3/2001 |
| WO | WO 01/16276 A1 | 3/2001 |
| WO | WO 01/16277 A1 | 3/2001 |
| WO | WO 02/42740 A1 | 5/2002 |
| WO | WO 02/062973 A2 | 8/2002 |
| WO | WO 2004/053039 A2 | 6/2004 |
| WO | WO 2004/101759 A2 | 11/2004 |
| WO | WO 2004/101760 A2 | 11/2004 |
| WO | WO 2004/101763 A2 | 11/2004 |
| WO | WO 2005/047264 A1 | 5/2005 |
| WO | WO 2006/125437 A2 | 11/2006 |
| WO | WO 2007/001262 A1 | 1/2007 |
| WO | WO 2007/087242 A2 | 8/2007 |

OTHER PUBLICATIONS

Chiou, H., "A Method to Reduce the Radial Resistivity Gradient of (111) As-Grown Silicon Crystals," Motorola, Inc., Technical Developments, IP.com Publication IP 6443D, vol. 15, 1992, p. 120.

Davis, F., et al., "Chemistry of Oxaziridines. 13 Synthesis, Reactions, and Properties of 3-Substituted 1,2 Benzisothiazole 1,1-Dioxide Oxides," J. Org: Chemistry, vol. 55, 1990, pp. 1254-1261.

Hanquet, G., et al., "Reaction of Paranitroperbenzoic Acid with N-Methyl-3, 4-Dihydroisoquinolinium Tetraflouroborate. Formation of an Oxaziridinium Salt," Tetrahedron, vol. 49, No. 2, 1993, pp. 423-438.

Hanquet, G., et al., "Peracid Oxidation of an Immonium Fluoroborate a New Example of Oxaziridium Salt," Tetrahedron Letters, vol. 28, No. 48, 1987, pp. 6061-6064.

Jennings, W., et al., "Optically Active N-Phosphinoyloxaziridines: Preparation and Chiral Oxygen Transfer to Prochiral Sulfides," J. Chem. Soc. Chem Commun., vol. 22, 1994, pp. 2569-2570.

Mohamed, M., et al., "Experimental and Theoretical Studies on Pyrolysis of O-Acetyl Derivatives of B-Phenylcinnamaldehyde and Benzaldehyde Oximes," Polish J. Chem., vol. 77, 2003, pp. 577-590.

Needleman, S., et al., "A General Method Applicable to the Search for Similarities in the Amino Acid Sequence of Two Proteins," J. Mol. Biol., vol. 48, 1970, pp. 443-453.

Van Ee, J., et al., "Application of Lipases in Detergents," Enzymes in Detergency, Chapters 6-7, 1997, pp. 93-132.

International Search Report in connection with PCT/US2007/001593, mailed on Aug. 3, 2007, pp. 1-4.

* cited by examiner

Figure 1                    Page 1 of figure

```
ID NO 1:    SSSSTQDYRIASEAEIKAHTFYTALSANA
ID NO 2:    SSSTQDYRIASEAEIKAHTFYTALSANA
ID NO 3:    SIDGGIRAATSQEINELTYYTTLSANS
ID NO 4:    SASDGGKVVAATTAQIQEFTKYAGIAATA
ID NO 5:        TAGHALAASTQ GISEDLYSRL VEMATISQAA
ID NO 6:        TAGHALAASTQ GISEDLYSRL VEMATISQAA
ID NO 7:            AVGVTTTDFSNFKFYIQHGAAA
ID NO 8:            TVTTQDLSNFRFYLQHADAA
ID NO 9:            DIPTTQLEDFKFWVQYAAAT
ID NO 10:           DVSTSELDQFEFWVQYAAAS
ID NO 11:           SVSTSTLDELQLFAQWSAAA
ID NO 12:           SVSTSTLDELQLFSQWSAAA
ID NO 13:           DVSSSLLNNLDLFAQYSAAA
ID NO 14:           EVSQDLFNQFNLFAQYSAAA
ID NO 15:           PQDAYTASHADLVKYATYAGLA

ID NO 1:    YCRTVIPG        GRWSCPHCGVAS    NLQITKTFST   LITDTNVLVAV
ID NO 2:    YCRTVIPG        GQWSCPHCDVAP    NLNITKTFTT   LITDTNVLVAV
ID NO 3:    YCRTVIPG        ATWDCIHCDATE    DLKIIKTWST   LIYDTNAMVAR
ID NO 4:    YCRSVVPG        NKWDCVQCQKWVP   DGKIITTFTS   LLSDTNGYVLR
ID NO 5:    YADLCNIPST                      IIKGEKIYNSQTDINGWILR
ID NO 6:    YADLCNIPST                      IIKGEKIYNSQTDINGWILR
ID NO 7:    YC    NSEAAA  GSKITCSNNGCPTVQGNGATIVTSF    VGSKTGIGGYVAT
ID NO 8:    YC    NFNTAV  GKPVHCSAGNCPDIEKDAAIVVGSV    VGTKTGIGAYVAT
ID NO 9:    YCPNNYVAKD GEKLNCSVGNCPDVEAAGSTVKLSFS      DDTITDTAGFVAV
ID NO 10:   YYEADYTAQV GDKLSCSKGNCPEVEATGATVSYDFS      DSTITDTAGYIAV
ID NO 11:   YCSNNID SK DSNLTCTANACPSVEEASTTMLLEFDLTNDFGGTAGFLAA
ID NO 12:   YCSNNID SD DSNVTCTADACPSVEEASTKMLLEFDLTNNFGGTAGFLAA
ID NO 13:   YCDENLN ST GTKLTCSVGNCPLVEAASTQSLDEFNESSSYGNPAGYLAA
ID NO 14:   YCGKNNDAPA GTNITCTGNACPEVEKADATFLYSFE DSGVGDVTGFLAL
ID NO 15:   YQTTDAWPAS              RTVPKDTTLISSFD    HTLKGSSGYIAF

ID NO 1:    GEKEKTIYVV FRGTSSIRNA IADIVFVPVN YPPV    NGA KVHKGFLDSY
ID NO 2:    GENEKTIYVV FRGTSSIRNA IADIVFVPVN YPPV    NGA KVHKGFLDSY
ID NO 3:    GDSEKTIYIV FRGSSSIRNW IADLTFVPVS YPPV    SGT KVHKGFLDSY
ID NO 4:    SDKQKTIYLV FRGTNSFRSA ITDIVFNFSD YKPV    KGA KVHAGFLSSY
ID NO 5:    DDSSKEIITV FRGTGSDTNL QLDTNYTLTP FDTLPQCNGC EVHGGYYIGW
ID NO 6:    DDSSKEIITV FRGTGSDTNL QLDTNYTLTP FDTLPQCNSC EVHGGYYIGW
ID NO 7:    DSARKEIVVS FRGSINIRNW LTNLDFG QE DCSL   VSGC GVHSGFQRAW
ID NO 8:    DNARKEIVVS VRGSINVRNW ITNFNFG QK TCDL   VAGC GVHTGFLDAW
ID NO 9:    DNTNKAIVVA FRGSYSIRNW VTDATFP QT DPGL   CDGC KAELGFWTAW
ID NO 10:   DHTNSAVVLA FRGSYSVRNW VADATFV HT NPGL   CDGC LAELGFWSSW
ID NO 11:   DNTNKRLVVA FRGSSTIENW IANLDFILED NDDL   CTGC KVHTGFWKAW
ID NO 12:   DNTNKRLVVA FRGSSTIKNW IADLDFILQD NDDL   CTGC KVHTGFWKAW
ID NO 13:   DETNKLLVLS FRGSADLANW VANLNFGLED ASDL   CSGC EVHSGFWKAW
ID NO 14:   DNTNKLIVLS FRGSRSIENW IGNLNFDLKE INDI   CSGC RGHDGFTSSW
ID NO 15:   NEPCKEIIVA YRGTDSLIDW LTNLNFDKTA WPAN   ISNS LVHEGFLNAY

ID NO 1:    NEVQDKLVAE VKAQLDRHPG YKIVVTGHSL GGATAVLSALDLYHHGHA
ID NO 2:    NEVQDKLVAE VKAQLDRHPG YKIVVTGHSL GGATAVLSALDLYHHGHD
ID NO 3:    GEVQNELVAT VLDQFKQYPS YKVAVTGHSL GGATALLCALDLYQREEGLS
ID NO 4:    EQVVNDYFPV VQEQLTAHPT YKVIVTGHSL GGAQALLAGMDLYQREPRLS
ID NO 5:    VSVQDQVESL VKQQVSQYPD YALTVTGHSL GASLAALTAAQL SATYD
ID NO 6:    ISVQDQVESL VQQQVSQFPD YALTVTGHSL GASLAALTAAQL SATYD
ID NO 7:    NEISSQATAA VASARKANPS FNVISTGHSL GGAVAVLAAANLRVGGT
ID NO 8:    EEVAANVKAA VSAAKTANPT FKFVVTGHSL GGAVATIAAAYLRKDGF
ID NO 9:    KVVRDRIIKT LDELKPEHSD YKIVVVGHSL GAAIASLAAADLRTKNY
ID NO 10:   KLVRDDIIKE LKEVVAQNPN YELVVVGHSL GAAVATLAATDLRGKGYP
ID NO 11:   ESAADELTSK IKSAMSTYSG YTLYFTGHSL GGALATLGATVLRNDGY
ID NO 12:   EAAADNLTSK IKSAMSTYSG YTLYFTGHSL GGALATLGATVLRNDGY
ID NO 13:   SEIADTITSK VESALSDHSD YSLVLTGHSY GAALAALAATALRNSGH
```

Figure 1            Page 2 of figure

```
ID NO 14:  RSVADTLRQK VEDAVREHPD YRVVFTGHSL GGALATVAGADLRGNGY
ID NO 15:  LVSMQQVQEA VDSLLAKCPD ATISFTGHSL GGALACISMVDTAQRHRGI

ID NO 1:      NIEIYTQG QPRIGTPAFA NYVIGT        KIPYQRLVHERDIVPHL
ID NO 2:      NIEIYTQG QPRIGTPEFA NYVIGT        KIPYQRLVNERDIVPHL
ID NO 3:      SSNLFLYTQG QPRVGDPAFA NYVVST      GIPYRRTVNERDIVPHL
ID NO 4:      PKNLSIFTVG GPRVGNPTFA YYVEST      GIPFQRTVHKRDIVPHV
ID NO 5:      NIRLYTFG EPRSGNQAFA SYMNDAFQASSPDTTQYFRVTHANDGIPNL
ID NO 6:      NIRLYTFG EPRS NQAFA SYMNDAFQASSPDTTQYFRVTHANDGIPNL
ID NO 7:      PVDIYTYG SPRVGNAQLS AFVSNQ        AGGEYRVTHADDPVPRL
ID NO 8:      PFDLYTYG SPRVGNDFFA NFVTQQ        TGAEYRVTHGDDPVPRL
ID NO 9:      DAILYAYA APRVANKPLA EFITNQ        GNNYRFTHNDDPVPKL
ID NO 10:     SAKLYAYA SPRVGNAALA KYITAQ        GNNFRFTHTNDPVPKL
ID NO 11:     SVELYTYG CPRIGNYALA EHITSQ        GSGANFRVTHLNDIVPRV
ID NO 12:     SVELYTYG CPRVGNYALA EHITSQ        GSGANFPVTHLNDIVPRV
ID NO 13:     SVELYNYG QPRLGNEALA TYITDQ        NKGGNYRVTHTNDIVPKL
ID NO 14:     DIDVFSYG APRVGNRAFA EFLTVQ        TGGTLYRITHTNDIVPRL
ID NO 15:     KMQMFTYG QPRTGNQAFA EYVENL        GHPVFRVVYRHDIVPRM

ID NO 1:   PPGAFGFLHA GEEFWIMK            DSSLRVCPNGIETDNCSNSIV
ID NO 2:   PPGAFGFLHA GEEFWIMK            DSSLRVCPNGIETDNCSNSIV
ID NO 3:   PPAAFGFLHA GEEYWITD            NSPETVQVCTSDLETSDCSNSIV
ID NO 4:   PPQSFGFLHP GVESWIKS            GTSNVQICTSEIETKDCSNSIV
ID NO 5:   PPVEQGYAHG GVEYWSV    DPYSAQNTFVCTGDEVQCCE AQGGQG
ID NO 6:   PPADEGYAHG VVEYWSV    DPYSAQNTFVCTGDEVQCCE AQGGQG
ID NO 7:   PPLIFGYRHT TPEFWLSGGGGDKVDYTISDVKVCEGAANLG CNGGTL
ID NO 8:   PPIVFGYRHT SPEYWLNG GPLDKDYTVTEIKVCEGIANVM CNGGTI
ID NO 9:   PLLTMGYVHI SPEYYITA  PDNTTVTDNQVTVLDGYVNFK GNTGTS
ID NO 10:  PLLSMGYVHV SPEYWITS  PNNATVSTSDIKVIDGDVSFD GNTGTG
ID NO 11:  PPMDFGFSQP SPEYWITS  GNGASVTASDIEVIEGINSTA GNAGEA
ID NO 12:  PPMDFGFSQP SPEYWITS  GTGASVTASDIELIEGINSTA GNAGEA
ID NO 13:  PPTLLGYHHF SPEYYISS  ADEATVTTTDVTEVTGIDATG GNDGTD
ID NO 14:  PPREFGYSHS SPEYWIKS  GTLVPVTRNDIVKIEGIDATG GNNQPN
ID NO 15:  PPMDLGFQHH GQEVWYEG            DENIKFCKGEGENLTCELGVP

ID NO 1:   PFT  SVIDHLSYLDMNTGL CL
ID NO 2:   PFT  SVIDHLSYLDMNTGL CL
ID NO 3:   PFT  SVLDHLSYFGINTGL CT
ID NO 4:   PFT  SILDHLSYFDINEGS CL
ID NO 5:   VN   NAHTTYF GMTSGACTW
ID NO 6:   VN   NAHTTYF GMTSGHCTW
ID NO 7:   GL   DIAAHLHYF QATDA CNAGGFSWR R
ID NO 8:   GL   DILAHITYF QSMAT CAPIAIPWK R
ID NO 9:   GGLPDLLAFHSHVWYFIHADACKGPGLPLR
ID NO 10:  LPLLTDFEAHIWYF VQVDA GKGPGLPFK R
ID NO 11:  TV   SVLAHLWYF FAISE CLL
ID NO 12:  TV   DVLAHLWYF FAISE CLL
ID NO 13:  GT   SIDAHRWYF IYISE CS
ID NO 14:  IP   DIPAHLWYF GLIGT CL
ID NO 15:  FSEL NAKDHSEYP GMH
```

| ID NO: | Micro organism | SEQ ID NO.: |
|---|---|---|
| 1. | *Absidia reflexa* | 3 |
| 2. | *Absidia corymbifera* | 4 |
| 3. | *Rhizmucor miehei* | 5 |
| 4. | *Rhizopus delemar (oryzea)* | 6 |
| 5. | *Aspergillus niger* | 7 |
| 6. | *Aspergillus tubingensis* | 8 |
| 7. | *Fusarium oxysporum* | 9 |
| 8. | *Fusarium heterosporum* | 10 |
| 9. | *Aspergillus oryzae* | 11 |
| 10. | *Penicilium camembertii* | 12 |

Figure 1                         Page 3 of figure

| | | |
|---|---|---|
| 11. | *Aspergillus foetidus* | 13 |
| 12 | *Aspergillus niger* | 14 |
| 13. | *Aspergillus oryzea* | 15 |
| 14. | *Thermomyces lanuginosus* | 2 |
| 15. | *Landerina penisapora* | 16 |

Figure 1. Alignment of lipase sequences.

US 7,786,067 B2

COMPOSITION COMPRISING A LIPASE AND A BLEACH CATALYST

CROSS-REFERENCES TO RELATED APPLICATIONS

This application claims priority under 35 U.S.C. §119(e) to U.S. Provisional Application Ser. No. 60/761,115 filed Jan. 23, 2006, U.S. Provisional Application Ser. No. 60/796,324 filed Apr. 28, 2006, and U.S. Provisional Application Ser. No. 60/854,835 filed Oct. 27, 2006.

FIELD OF THE INVENTION

The present invention relates to a composition comprising a lipase and a bleach catalyst. More specifically, the present invention relates to composition comprising a lipase and a bleach catalyst that is capable of accepting an oxygen atom from a peroxyacid and transferring the oxygen atom to an oxidizeable substrate. The compositions of the present invention are typically suitable for use as laundry detergent compositions and exhibit a good cleaning performance and a reduced malodor profile, especially on problematic residual dairy soils.

BACKGROUND OF THE INVENTION

Dingy soils such as body soils and other hydrophobic soils, including dairy soils, are extremely difficult to remove from fabric during a laundering process. The appearance of lipase enzymes suitable for detergent applications in the 1980's (e.g. Lipolase and Lipolase Ultra, ex Novo Nordisk—now Novozymes) gave the formulator a new approach to improve grease removal. Lipase enzymes catalyse the hydrolysis of triglycerides which form a major component of many commonly encountered fatty soils such as sebum, animal fats (e.g. lard, ghee, butter) and vegetable oils (e.g. olive oil, sunflower oil, peanut oil). However, these enzymes show limited performance in the first wash cycle (being effective mainly during the drying stage of the laundering process) and give rise to a post-wash malodor. Without wishing to be bound by theory, the malodor arises from fatty acids released by the hydrolysis of fats and is particularly noticeable for dairy soils like milk, cream, butter and yogurt; dairy fats contain triglycerides functionalized with short chain (e.g. $C_4$) fatty acyl units which release malodorous volatile fatty acids after lipolysis. For a general review of the use of lipases in solid laundry detergents see the following reference: Enzymes in Detergency, ed. J. H. van Ee et al, Vol 69 Marcel Dekker Surfactant Series, Marcel Dekker, New York, 1997, pp 93-132 (ISBN 0-8247-9995-X).

More recently so-called 'first wash' lipases have been commercialised such as Lipoprime™ and Lipex™ (ex. Novozymes) which show performance benefits in the initial wash cycle. The Lipex™ enzyme is described in more detail in WO 00/60063 and U.S. Pat. No. 6,939,702 B1 (Novozymes). Laundry detergent formulations comprising the Lipex™ enzyme are described in more detail in IP.com publication IP 6443D (Novozymes). However in order to better exploit lipase technology, both the odour profile on residual dairy stains and the cleaning performance on complex soils still needs to be improved.

Detergent manufacturers have also attempted to incorporate bleach catalysts, especially oxaziridium or oxaziridinium-forming bleach catalysts, in their detergent products in an attempt to provide a good bleaching performance. EP 0 728 181, EP 0 728 182, EP 0 728 183, EP 0 775 192, U.S. Pat. No. 4,678,792, U.S. Pat. No. 5,045,223, U.S. Pat. No. 5,047,163, U.S. Pat. No. 5,360,568, U.S. Pat. No. 5,360,569, U.S. Pat. No. 5,370,826, U.S. Pat. No. 5,442,066, U.S. Pat. No. 5,478,357, U.S. Pat. No. 5,482,515, U.S. Pat. No. 5,550,256, U.S. Pat. No. 5,653,910, U.S. Pat. No. 5,710,116, U.S. Pat. No. 5,760,222, U.S. Pat. No. 5,785,886, U.S. Pat. No. 5,952,282, U.S. Pat. No. 6,042,744, WO95/13351, WO95/13353, WO97/10323, WO98/16614, WO00/42151, WO00/42156, WO01/16110, WO01/16263, WO01/16273, WO01/16274, WO01/16275, WO01/16276, WO01/16277 relate to detergent compositions comprising an oxaziriduium and/or an oxaziridinium-forming bleach catalyst.

There is a continuing need for laundry detergent compositions that exhibit a good overall cleaning profile, a good cold water temperature bleaching performance, good greasy soil cleaning performance and a reduced malodor profile on residual fatty soils, especially dairy soils.

The Inventors have found that by using lipase in combination with a bleach catalyst that is capable of accepting an oxygen atom from a peroxyacid and transferring the oxygen atom to an oxidizeable substrate improves the cleaning performance of the detergent composition whilst maintaining a reduced malodor profile on residual fatty soils, especially dairy soils.

In another embodiment of the present invention, the Inventors have found that the rubber sump hose compatibility profile is improved when a diacyl and/or a tetraacyl peroxide species is in combination with a lipase.

In an especially preferred embodiment of the present invention, the Inventors have found that using a lipase in combination with (i) a bleach catalyst that is capable of accepting an oxygen atom from a peroxyacid and transferring the oxygen atom to an oxidizeable substrate and (ii) a diacyl and/or tetraacyl peroxide species, significantly improves the cleaning performance of the composition, reduces the malodor profile of the composition and improves the rubber sump hose compatibility profile of the composition.

BRIEF DESCRIPTION OF THE FIGURES

FIG. 1 shows the alignment of lipases.

SEQUENCE LISTINGS

SEQ ID NO: 1 shows the DNA sequence encoding lipase from *Thermomyces lanoginosus*.

SEQ ID NO: 2 shows the amino acid sequence of a lipase from *Thermomyces lanoginosus*.

SEQ ID NO: 3 shows the amino acid sequence of a lipase from *Absidia reflexa*.

SEQ ID NO: 4 shows the amino acid sequence of a lipase from *Absidia corymbifera*.

SEQ ID NO: 5 shows the amino acid sequence of a lipase from *Rhizomucor miehei*.

SEQ ID NO: 6 shows the amino acid sequence of a lipase from *Rhizopus oryzae*.

SEQ ID NO: 7 shows the amino acid sequence of a lipase from *Aspergillus niger*.

SEQ ID NO: 8 shows the amino acid sequence of a lipase from *Aspergillus tubingensis*.

SEQ ID NO: 9 shows the amino acid sequence of a lipase from *Fusarium oxysporrum*.

SEQ ID NO: 10 shows the amino acid sequence of a lipase from *Fusarium heterosporum*.

SEQ ID NO: 11 shows the amino acid sequence of a lipase from *Aspergillus oryzae*.

SEQ ID NO: 12 shows the amino acid sequence of a lipase from *Penicillium camemberti*.

SEQ ID NO: 13 shows the amino acid sequence of a lipase from *Aspergillus foetidus*.

SEQ ID NO: 14 shows the amino acid sequence of a lipase from *Aspergillus niger*.

SEQ ID NO: 15 shows the amino acid sequence of a lipase from *Aspergillus oryzae*.

SEQ ID NO: 16 shows the amino acid sequence of a lipase from *Landerina penisapora*.

SUMMARY OF THE INVENTION

In a first embodiment, the present invention provides a composition comprising: (i) a lipase; and (ii) a bleach catalyst that is capable of accepting an oxygen atom from a peroxyacid and transferring the oxygen atom to an oxidizeable substrate.

In a second embodiment, the present invention provides a composition comprising: (i) a lipase; and (ii) a diacyl and/or tetraacyl peroxide species.

DETAILED DESCRIPTION OF THE INVENTION

Composition

The composition comprises: (i) a lipase; and (ii) a bleach catalyst that is capable of accepting an oxygen atom from a peroxyacid and transferring the oxygen atom to an oxidizeable substrate. The lipase and the bleach catalyst are described in more detail below.

The composition may be suitable for use as a laundry detergent composition, laundry additive composition, dishwashing composition, or hard surface cleaning composition. The composition is typically a detergent composition. The composition may be a fabric treatment composition. Preferably the composition is a laundry detergent composition.

The composition can be any form such as liquid or solid, although preferably the composition is in solid form. Typically, the composition is in particulate form such as an agglomerate, a spray-dried powder, an extrudate, a flake, a needle, a noodle, a bead, or any combination thereof. The composition may be in compacted particulate form, such as in the form of a tablet or bar. The composition may be in some other unit dose form, such as in the form of a pouch, wherein the composition is typically at least partically, preferably essentially completely, enclosed by a water-soluble film such as polyvinyl alcohol. Preferably, the composition is in free-flowing particulate form; by free-flowing particulate form, it is typically meant that the composition is in the form of separate discrete particles. The composition may be made by any suitable method including agglomeration, spray-drying, extrusion, mixing, dry-mixing, liquid spray-on, roller compaction, spheronisation, tabletting or any combination thereof.

The composition typically has a bulk density of from 450 g/l to 1,000 g/l, preferred low bulk density detergent compositions have a bulk density of from 550 g/l to 650 g/l and preferred high bulk density detergent compositions have a bulk density of from 750 g/l to 900 g/l. The composition may also have a bulk density of from 650 g/l to 750 g/l. During the laundering process, the composition is typically contacted with water to give a wash liquor having a pH of from above 7 to less than 13, preferably from above 7 to less than 10.5. This is the optimal pH to provide good cleaning whilst also ensuring a good fabric care profile.

Preferably, the composition comprises: (i) from 0% to less than 10%, preferably to 7%, or to 4%, or from 1%, or from 1.5%, by weight of the composition, of tetraacetylethylenediamine and/or oxybenzene sulphonate bleach activators. Most preferably, the composition is essentially free of tetraacetylethylenediamine and/or oxybenzene sulphonate bleach activators. By "is essential free of" it is typically meant "comprises no deliberately incorporated". Keeping the levels of these types of bleach activators to a minimum maintains the good dye safety profile of the composition.

Preferably, upon contact with water the composition forms a wash liquor having a pH of from 7 to 10.5. Compositions having this reserve alkalinity profile and pH profile exhibit a good stability profile for lipase.

Preferably, the composition comprises from 0% or from 1%, or from 2%, or from 3%, or from 4%, or from 5%, and to 30%, or to 20%, or to 10%, by weight of the composition, of a source of carbonate anion. The above described levels of a source of carbonate anion ensure that the composition has a good overall cleaning performance and a good bleaching performance.

Preferably, the composition comprises a dye transfer inhibitor. Suitable dye transfer inhibitors are selected from the group consisting of: polyvinylpyrrolidone, preferably having a weight average molecular weight of from 40,000 Da to 80,000 Da, preferably from 50,000 D1 to 70,000 Da; polyvinylimidazole, preferably having a weight average molecular weight of from 10,000 Da to 40,000 Da, preferably from 15,000 Da to 25,000 Da; polyvinyl pyridine N-oxide polymer, preferably having a weight average molecular weight of from 30,000 Da to 70,000 Da, preferably from 40,000 Da to 60,000 Da; a co-polymer of polyvinylpyrrolidone and vinyl imidazole, preferably having a weight average molecular weight of from 30,000 Da to 70,000 Da, preferably from 40,000 Da to 60,000 Da; and any combination thereof. Compositions comprising a dye transfer inhibitor show a further improved dye safety profile.

The composition may comprise from 0% to less than 5%, preferably to 4%, or to 3%, or to 2%, or even to 1%, by weight of the composition, of zeolite-builder. Whilst the composition may comprise zeolite-builder at a level of 5 wt % or greater, preferably the composition comprises less than 5 wt % zeolite-builder. It may be preferred for the composition to be essentially free of zeolite-builder. By: "essentially free of zeolite-builder", it is typically meant that the composition comprises no deliberately incorporated zeolite-builder. This is especially preferred when the composition is a solid laundry detergent composition and it is desirable for the composition to be very highly soluble, to minimize the amount of water-insoluble residues (for example, which may deposit on fabric surfaces), and also when it is highly desirable to have transparent wash liquor. Suitable zeolite-builders include zeolite A, zeolite X, zeolite P and zeolite MAP.

The composition may comprise from 0% to less than 10%, or less than 5%, preferably to 4%, or to 3%, or to 2%, or even to 1%, by weight of the composition, of phosphate-builder. Whilst the composition may comprise phosphate-builder at a level of 10 wt % or greater, preferably the composition comprises less than 10 wt % phosphate-builder. It may even be preferred for the composition to be essentially free of phosphate-builder. By: "essentially free of phosphate-builder", it is typically meant that the composition comprises no deliberately added phosphate-builder. This is especially preferred if it is desirable for the composition to have a very good environmental profile. Suitable phosphate-builders include sodium tripolyphosphate.

The composition may comprise from 0% to less than 5%, or preferably to 4%, or to 3%, or even to 2%, or to 1%, by weight of the composition, of silicate salt. Whilst the composition may comprise silicate salt at a level of 5 wt % or greater, preferably the composition comprises less than 5 wt % silicate salt. It may even be preferred for the composition to be essentially free of silicate salt. By: "essentially free from silicate salt", it is typically meant that the composition comprises no deliberately added silicate salt. This is especially preferred when the composition is a solid laundry detergent composition and it is desirable to ensure that the composition has very good dispensing and dissolution profiles and to ensure that the composition provides a clear wash liquor upon dissolution in water. The silicate salts include water-insoluble silicate salts. The silicate salts also include amorphous silicate salts and crystalline layered silicate salts (e.g. SKS-6). The silicate salts include sodium silicate.

The composition typically comprises adjunct ingredients. These adjunct ingredients include: detersive surfactants such as anionic detersive surfactants, non-ionic detersive surfactants, cationic detersive surfactants, zwitterionic detersive surfactants, amphoteric detersive surfactants; preferred anionic detersive surfactants are alkoxylated anionic detersive surfactants such as linear or branched, substituted or unsubstituted $C_{12-18}$ alkyl alkoxylated sulphates having an average degree of alkoxylation of from 1 to 30, preferably from 1 to 10, more preferably a linear or branched, substituted or unsubstituted $C_{12-18}$ alkyl ethoxylated sulphates having an average degree of ethoxylation of from 1 to 10, most preferably a linear unsubstituted $C_{12-18}$ alkyl ethoxylated sulphates having an average degree of ethoxylation of from 3 to 7, other preferred anionic detersive surfactants are alkyl sulphates, alkyl sulphonates, alkyl phosphates, alkyl phosphonates, alkyl carboxylates or any mixture thereof, preferred alkyl sulphates include linear or branched, substituted or unsubstituted $C_{10-18}$ alkyl sulphates, another preferred anionic detersive surfactant is a $C_{10-13}$ linear alkyl benzene sulphonate; preferred non-ionic detersive surfactants are $C_{8-18}$ alkyl alkoxylated alcohols having an average degree of alkoxylation of from 1 to 20, preferably from 3 to 10, most preferred are $C_{12-18}$ alkyl ethoxylated alcohols having an average degree of alkoxylation of from 3 to 10; preferred cationic detersive surfactants are mono-$C_{6-18}$ alkyl mono-hydroxyethyl di-methyl quaternary ammonium chlorides, more preferred are mono-$C_{8-10}$ alkyl mono-hydroxyethyl di-methyl quaternary ammonium chloride, mono-$C_{10-12}$ alkyl mono-hydroxyethyl di-methyl quaternary ammonium chloride and mono-$C_{10}$ alkyl mono-hydroxyethyl di-methyl quaternary ammonium chloride; source of peroxygen such as percarbonate salts and/or perborate salts, preferred is sodium percarbonate, the source of peroxygen is preferably at least partially coated, preferably completely coated, by a coating ingredient such as a carbonate salt, a sulphate salt, a silicate salt, borosilicate, or mixtures, including mixed salts thereof; bleach activators such as tetraacetyl ethylene diamine, oxybenzene sulphonate bleach activators such as nonanoyl oxybenzene sulphonate, caprolactam bleach activators, imide bleach activators such as N-nonanoyl-N-methyl acetamide; enzymes such as amylases, arabinases, xylanases, galactanases, glucanases, carbohydrases, cellulases, laccases, oxidases, peroxidases, proteases, glucanases, pectate lyases and mannanases, especially preferred are proteases; suds suppressing systems such as silicone based suds suppressors; fluorescent whitening agents; photobleach; filler salts such as sulphate salts, preferably sodium sulphate; fabric-softening agents such as clay, silicone and/or quaternary ammonium compounds, especially preferred is montmorillonite clay optionally in combination with a silicone; flocculants such as polyethylene oxide; dye transfer inhibitors such as polyvinylpyrrolidone, poly 4-vinylpyridine N-oxide and/or co-polymer of vinylpyrrolidone and vinylimidazole; fabric integrity components such as hydrophobically modified cellulose and oligomers produced by the condensation of imidazole and epichlorhydrin; soil dispersants and soil anti-redeposition aids such as alkoxylated polyamines and ethoxylated ethyleneimine polymers; anti-redeposition components such as carboxymethyl cellulose and polyesters; perfumes; sulphamic acid or salts thereof; citric acid or salts thereof; carbonate salts, especially preferred is sodium carbonate; and dyes such as orange dye, blue dye, green dye, purple dye, pink dye, or any mixture thereof.

A second embodiment of the present invention relates to a composition comprising: (i) a lipase; and (ii) a diacyl peroxide.

Lipase

The lipase of the composition of the present invention is a lipase variant with no C-terminal extension but with mutations introduced in certain regions of a parent lipase whereby the tendency to odor generation is reduced.

Parent Lipase

The parent lipase may be a fungal lipase with an amino acid sequence having at least 50% homology as defined in the section "Homology and aligment" to the sequence of the *T. lanuginosus* lipase shown in SEQ ID NO: 2.

The parent lipase may be a yeast polypeptide such as a *Candida*, *Kluyveromyces*, *Pichia*, *Saccharomyces*, *Schizosaccharomyces*, or *Yarrowia* polypeptide; or more preferably a filamentous fungal polypeptide such as an *Acremonium*, *Aspergillus*, *Aureobasidium*, *Cryptococcus*, *Filobasidium*, *Fusarium*, *Humicola*, *Magnaporthe*, *Mucor*, *Myceliophthora*, *Neocallimastix*, *Neurospora*, *Paecilomyces*, *Penicillium*, *Piromyces*, *Schizophyllum*, *Talaromyces*, *Thermoascus*, *Thielavia*, *Tolypocladium*, or *Trichoderma* polypeptide.

In a preferred aspect, the parent lipase is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, or *Saccharomyces oviformis* polypeptide having lipase activity.

In another preferred aspect, the parent lipase is an *Aspergillus aculeatus*, *Aspergillus awamori*, *Aspergillus fumigatus*, *Aspergillus foetidus*, *Aspergillus japonicus*, *Aspergillus nidulans*, *Aspergillus niger*, *Aspergillus oryzae*, *Aspergillus turbigensis*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola insolens*, *Thermomyces lanoginosus* (synonym: *Humicola lanuginose*), *Mucor miehei*, *Myceliophthora thermophila*, *Neurospora crassa*, *Penicillium purpurogenum*, *Trichoderma harzianum*, *Trichoderma koningii*, *Trichoderma longibrachiatum*, *Trichoderma reesei*, or *Trichoderma viride* polypeptide.

In another preferred aspect, the parent lipase is a *Thermomyces* lipase.

In a more preferred aspect, the parent lipase is a *Thermomyces lanuginosus* lipase. In an even more preferred embodiment the parent lipase is the lipase of SEQ ID NO: 2.

Identification of Regions and Substitutions.

The positions referred to in Region I through Region IV below are the positions of the amino acid residues in SEQ ID NO:2. To find the corresponding (or homologous) positions in a different lipase, the procedure described in "Homology and alignment" is used.

Substitutions in Region I

Region I consists of amino acid residues surrounding the N-terminal residue E1. In this region it is preferred to substitute an amino acid of the parent lipase with a more positive amino acid. Amino acid residues corresponding to the following positions are comprised by Region I: 1 to 11 and 223-239. The following positions are of particular interest: 1, 2, 4, 8, 11, 223, 227, 229, 231, 233, 234 and 236. In particular the following substitutions have been identified: X1N/*, X4V, X227G, X231R and X233R.

In a preferred embodiment the parent lipase has at least 80%, such as 85% or 90%, such as at least 95% or 96% or 97% or 98% or 99%, identity to SEQ ID NO:2. In a most preferred embodiment the parent lipase is identical to SEQ ID NO: 2.

Substitutions in Region II

Region II consists of amino acid residues in contact with substrate on one side of the acyl chain and one side of the alcohol part. In this region it is preferred to substitute an amino acid of the parent lipase with a more positive amino acid or with a less hydrophobic amino acid. Amino acid residues corresponding to the following positions are comprised by Region II: 202 to 211 and 249 to 269. The following positions are of particular interest: 202, 210, 211, 253, 254, 255, 256, 259. In particular the following substitutions have been identified: X202G, X210K/W/A, X255Y/V/A, X256K/R and X259G/M/Q/V.

In a preferred embodiment the parent lipase has at least 80%, such as 85% or 90%, such as at least 95% or 96% or 97% or 98% or 99%, identity to SEQ ID NO:2. In a most preferred embodiment the parent lipase is identical to SEQ ID NO: 2.

Substitutions in Region III

Region III consists of amino acid residues that form a flexible structure and thus allowing the substrate to get into the active site. In this region it is preferred to substitute an amino acid of the parent lipase with a more positive amino acid or a less hydrophobic amino acid. Amino acid residues corresponding to the following positions are comprised by Region III: 82 to 102. The following positions are of particular interest: 83, 86, 87, 90, 91, 95, 96, 99. In particular the following substitutions have been identified: X83T, X86V and X90A/R.

In a preferred embodiment the parent lipase has at least 80%, such as 85% or 90%, such as at least 95% or 96% or 97% or 98% or 99%, identity to SEQ ID NO:2. In a most preferred embodiment the parent lipase is identical to SEQ ID NO: 2.

Substitutions in Region IV

Region IV consists of amino acid residues that bind electrostatically to a surface. In this region it is preferred to substitute an amino acid of the parent lipase with a more positive amino acid. Amino acid residues corresponding to the following positions are comprised by Region IV: 27 and 54 to 62. The following positions are of particular interest: 27, 56, 57, 58, 60. In particular the following substitutions have been identified: X27R, X58N/AG/T/P and X60V/S/G/N/R/K/A/L.

In a preferred embodiment the parent lipase has at least 80%, such as 85% or 90%, such as at least 95% or 96% or 97% or 98% or 99%, identity to SEQ ID NO:2. In a most preferred embodiment the parent lipase is identical to SEQ ID NO: 2.

Amino Acids at Other Positions

The parent lipase may optionally comprise substitutions of other amino acids, particularly less than 10 or less than 5 such substitutions. Examples are substitutions corresponding to one or more of the positions 24, 37, 38, 46, 74, 81, 83, 115, 127, 131, 137, 143, 147, 150, 199, 200, 203, 206, 211, 263, 264, 265, 267 and 269 of the parent lipase. In a particular embodiment there is a substitution in at least one of the positions corresponding to position 81, 143, 147, 150 and 249. In a preferred embodiment the at least one substitution is selected from the group consisting of X81Q/E, X143S/C/N/D/A, X147M/Y, X150G/K and X249R/I/L.

The variant may comprise substitutions outside the defined Regions I to IV, the number of substitutions outside of the defined Regions I to IV is preferably less than six, or less than five, or less than four, or less than three, or less than two, such as five, or four, or three, or two or one. Alternatively, the variant does not comprise any substitution outside of the defined Regions I to IV.

Further substitutions may, e.g., be made according to principles known in the art, e.g. substitutions described in WO 92/05249, WO 94/25577, WO 95/22615, WO 97/04079 and WO 97/07202.

Parent Lipase Variants

In one aspect, said variant, when compared to said parent, comprising a total of at least three substitutions, said substitutions being selected from one or more of the following groups of substitutions:

a) at least two, or at least three, or at least four, or at least five, or at least six, such as two, three, four, five or six, substitutions in Region I, b) at least one, at least two, or at least three, or at least four, or at least five, or at least six, such as one, two, three, four, five or six, substitution in Region II, c) at least one, at least two, or at least three, or at least four, or at least five, or at least six, such as one, two, three, four, five or six, substitution in Region III, d) and/or at least one, at least two, or at least three, or at least four, or at least five, or at least six, such as one, two, three, four, five or six, substitution in Region IV.

The variant may comprise substitutions, compared to the variant's parent, corresponding to those substitutions listed below in Table 1.

TABLE 1

Some particular variants.

| Region I | Region II | Region III | Region IV | Outside regions |
|---|---|---|---|---|
| X4V + X227G + X231R + X233R | X210K + X256K | X83T + X86V | X58A + X60S | X150G |
| X227G + X231R + X233R | X256K | X86V | X58N + X60S | X150G |
| X231R + X233R | X255Y | | | |
| X231R + X233R | X202G | | | |

TABLE 1-continued

Some particular variants.

| Region I | Region II | Region III | Region IV | Outside regions |
|---|---|---|---|---|
| X227G + X231R + X233R | X256K | X86V | | |
| X4V + X231R + X233R | | | X58N + X60S | |
| X231R + X233R | | X90R | X58N + X60S | |
| X231R + X233R | X255V | X90A | | |
| X227G + X231R + X233R | X256K | X86V | X58N + X60S | X150G |
| X231R + X233R | X211L | | X58N + X60S | X147M |
| X231R + X233R | | | | X150K |

In a further particular embodiment the parent lipase is identical to SEQ ID NO:2, and the variants of Table 1 will thus be:

TABLE 2

Some particular variants of SEQ ID NO: 2

| Region I | Region II | Region III | Region IV | Outside regions |
|---|---|---|---|---|
| Q4V + L227G + T231R + N233R | E210K + P256K | S83T + I86V | S58A + V60S | A150G |
| L227G + T231R + N233R | P256K | I86V | S58N + V60S | A150G |
| T231R + N233R | I255Y | | | |
| T231R + N233R | I202G | | | |
| L227G + T231R + N233R | P256K | I86V | | |
| Q4V + T231R + N233R | | | S58N + V60S | |
| T231R + N233R | | I90R | S58N + V60S | |
| T231R + N233R | I255V | I90A | | |
| L227G + T231R + N233R | P256K | I86V | S58N + V60S | A150G |
| T231R + N233R | F211L | | S58N + V60S | L147M |
| X231R + X233R | | | | X150K |

Nomenclature for Amino Acid Modifications

In describing lipase variants according to the invention, the following nomenclature is used for ease of reference: Original amino acid(s):position(s):substituted amino acid(s)

According to this nomenclature, for instance the substitution of glutamic acid for glycine in position 195 is shown as G195E. A deletion of glycine in the same position is shown as G195*, and insertion of an additional amino acid residue such as lysine is shown as G195GK. Where a specific lipase contains a "deletion" in comparison with other lipases and an insertion is made in such a position this is indicated as *36D for insertion of an aspartic acid in position 36. Multiple mutations are separated by pluses, i.e.: R170Y+G195E, representing mutations in positions 170 and 195 substituting tyrosine and glutamic acid for arginine and glycine, respectively.

X231 indicates the amino acid in a parent polypeptide corresponding to position 231, when applying the described alignment procedure. X231R indicates that the amino acid is replaced with R. For SEQ ID NO:2 X is T, and X231R thus indicates a substitution of T in position 231 with R. Where the amino acid in a position (e.g. 231) may be substituted by another amino acid selected from a group of amino acids, e.g. the group consisting of R and P and Y, this will be indicated by X231R/P/Y.

In all cases, the accepted IUPAC single letter or triple letter amino acid abbreviation is employed.

Amino Acid Grouping

In this specification, amino acids are classified as negatively charged, positively charged or electrically neutral according to their electric charge at pH 10. Thus, negative amino acids are E, D, C (cysteine) and Y, particularly E and D. Positive amino acids are R, K and H, particularly R and K. Neutral amino acids are G, A, V, L, I, P, F, W, S, T, M, N, Q and C when forming part of a disulfide bridge. A substitution with another amino acid in the same group (negative, positive or neutral) is termed a conservative substitution.

The neutral amino acids may be divided into hydrophobic or non-polar (G, A, V, L, I, P, F, W and C as part of a disulfide bridge) and hydrophilic or polar (S, T, M, N, Q).

Amino Acid Identity

The relatedness between two amino acid sequences or between two nucleotide sequences is described by the parameter "identity".

For purposes of the present invention, the alignment of two amino acid sequences is determined by using the Needle program from the EMBOSS package (http://emboss.org) version 2.8.0. The Needle program implements the global alignment algorithm described in Needleman, S. B. and Wunsch, C. D. (1970) J. Mol. Biol. 48, 443-453. The substitution matrix used is BLOSUM62, gap opening penalty is 10, and gap extension penalty is 0.5.

The degree of identity between an amino acid sequence of the present invention ("invention sequence"; e.g. amino acids 1 to 269 of SEQ ID NO:2) and a different amino acid sequence ("foreign sequence") is calculated as the number of exact matches in an alignment of the two sequences, divided by the length of the "invention sequence" or the length of the "foreign sequence", whichever is the shortest. The result is expressed in percent identity.

An exact match occurs when the "invention sequence" and the "foreign sequence" have identical amino acid residues in the same positions of the overlap. The length of a sequence is the number of amino acid residues in the sequence (e.g. the length of SEQ ID NO:2 is 269).

The parent lipase has an amino acid identity of at least 50% with the *T. lanuginosus* lipase (SEQ ID NO: 2), particularly at least 55%, at least 60%, at least 75%, at least 85%, at least 90%, more than 95% or more than 98%. In a particular embodiment the parent lipase is identical to the *T. lanuginosus* lipase (SEQ ID NO:2).

The above procedure may be used for calculation of identity as well as homology and for alignment. In the context of the present invention homology and alignment has been calculated as described below.

Homology and Alignment

For purposes of the present invention, the degree of homology may be suitably determined by means of computer programs known in the art, such as GAP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443-45), using GAP with the following settings for polypeptide sequence comparison: GAP creation penalty of 3.0 and GAP extension penalty of 0.1.

In the present invention, corresponding (or homologous) positions in the lipase sequences of *Absidia reflexa, Absidia corymbefera, Rhizmucor miehei, Rhizopus delemar, Aspergillus niger, Aspergillus tubigensis, Fusarium oxysporum, Fusarium heterosporum, Aspergillus oryzae, Penicilium camembertii, Aspergillus foetidus, Aspergillus niger, Thermomyces lanoginosus* (synonym: *Humicola lanuginose*) and *Landerina penisapora* are defined by the alignment shown in FIG. 1.

To find the homologous positions in lipase sequences not shown in the alignment, the sequence of interest is aligned to the sequences shown in FIG. 1. The new sequence is aligned to the present alignment in FIG. 1 by using the GAP alignment to the most homologous sequence found by the GAP program. GAP is provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443-45). The following settings are used for polypeptide sequence comparison: GAP creation penalty of 3.0 and GAP extension penalty of 0.1.

The parent lipase has a homology of at least 50% with the *T. lanuginosus* lipase (SEQ ID NO: 2), particularly at least 55%, at least 60%, at least 75%, at least 85%, at least 90%, more than 95% or more than 98%. In a particular embodiment the parent lipase is identical to the *T. lanuginosus* lipase (SEQ ID NO:2).

Hybridization

The present invention also relates to isolated polypeptides having lipase activity which are encoded by polynucleotides which hybridize under very low stringency conditions, preferably low stringency conditions, more preferably medium stringency conditions, more preferably medium-high stringency conditions, even more preferably high stringency conditions, and most preferably very high stringency conditions with (i) nucleotides 178 to 660 of SEQ ID NO: 1, (ii) the cDNA sequence contained in nucleotides 178 to 660 of SEQ ID NO: 1, (iii) a subsequence of (i) or (ii), or (iv) a complementary strand of (i), (ii), or (iii) (J. Sambrook, E. F. Fritsch, and T. Maniatus, 1989, Molecular Cloning, A Laboratory Manual, 2d edition, Cold Spring Harbor, N.Y.). A subsequence of SEQ ID NO: 1 contains at least 100 contiguous nucleotides or preferably at least 200 contiguous nucleotides. Moreover, the subsequence may encode a polypeptide fragment which has lipase activity.

For long probes of at least 100 nucleotides in length, very low to very high stringency conditions are defined as prehybridization and hybridization at 42° C. in 5×SSPE, 0.3% SDS, 200 ug/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

DNA Sequence, Expression Vector, Host Cell, Production of Lipase

The invention provides a DNA sequence encoding the lipase of the invention, an expression vector harboring the DNA sequence, and a transformed host cell containing the DNA sequence or the expression vector. These may be obtained by methods known in the art.

The invention also provides a method of producing the lipase by culturing the transformed host cell under conditions conducive for the production of the lipase and recovering the lipase from the resulting broth. The method may be practiced according to principles known in the art.

-Lipase Activity

Lipase Activity on Tributyrin at Neutral pH (LU)

A substrate for lipase is prepared by emulsifying tributyrin (glycerin tributyrate) using gum Arabic as emulsifier. The hydrolysis of tributyrin at 30° C. at pH 7 or 9 is followed in a pH-stat titration experiment. One unit of lipase activity (1 LU) equals the amount of enzyme capable of releasing 1 micro mol butyric acid/min at pH 7.

-Benefit Risk

The Benefit Risk factor describing the performance compared to the reduced risk for odour smell is defined as: $BR=RP_{avg}/R$. Lipase variants described herein may have BRs greater than 1, greater than 1.1, or even greater than 1 to about 1000.

-Average Relative Performance

The procedure for calculating average relative performance (RPavg) is found in Example 5 of the present specification. Lipase variants described herein may have (RPavg) of at least 0.8, at least 1.1, at least 1.5, or even at least 2 to about 1000.

Bleach Catalyst

The bleach catalyst is capable of accepting an oxygen atom from a peroxyacid and/or salt thereof, and transferring the oxygen atom to an oxidizeable substrate. Suitable bleach catalysts include, but are not limited to: iminium cations and polyions; iminium zwitterions; modified amines; modified amine oxides; N-sulphonyl imines; N-phosphonyl imines; N-acyl imines; thiadiazole dioxides; perfluoroimines; cyclic sugar ketones and mixtures thereof.

Suitable iminium cations and polyions include, but are not limited to, N-methyl-3,4-dihydroisoquinolinium tetrafluoroborate, prepared as described in Tetrahedron (1992), 49(2), 423-38 (see, for example, compound 4, p. 433); N-methyl-3, 4-dihydroisoquinolinium p-toluene sulphonate, prepared as described in U.S. Pat. No. 5,360,569 (see, for example, Column 11, Example 1); and N-octyl-3,4-dihydroisoquinolinium p-toluene sulphonate, prepared as described in U.S. Pat. No. 5,360,568 (see, for example, Column 10, Example 3).

Suitable iminium zwitterions include, but are not limited to, N-(3-sulfopropyl)-3,4-dihydroisoquinolinium, inner salt, prepared as described in U.S. Pat. No. 5,576,282 (see, for example, Column 31, Example II); N-[2-(sulphooxy)dodecyl]-3,4-dihydroisoquinolinium, inner salt, prepared as described in U.S. Pat. No. 5,817,614 (see, for example, Column 32, Example V); 2-[3-[(2-ethylhexyl)oxy]-2-(sulphooxy)propyl]-3,4-dihydroisoquinolinium, inner salt, prepared as described in WO05/047264 (see, for example, page 18, Example 8), and 2-[3-[(2-butyloctyl)oxy]-2-(sulphooxy)propyl]-3,4-dihydroisoquinolinium, inner salt.

Suitable modified amine oxygen transfer catalysts include, but are not limited to, 1,2,3,4-tetrahydro-2-methyl-1-isoquinolinol, which can be made according to the procedures described in Tetrahedron Letters (1987), 28(48), 6061-6064. Suitable modified amine oxide oxygen transfer catalysts include, but are not limited to, sodium 1-hydroxy-N-oxy-N-[2-(sulphooxy)decyl]-1,2,3,4-tetrahydroisoquinoline.

Suitable N-sulphonyl imine oxygen transfer catalysts include, but are not limited to, 3-methyl-1,2-benzisothiazole 1,1-dioxide, prepared according to the procedure described in the Journal of Organic Chemistry (1990), 55(4), 1254-61.

Suitable N-phosphonyl imine oxygen transfer catalysts include, but are not limited to, [R-(E)]-N-[(2-chloro-5-nitrophenyl)methylene]-P-phenyl-P-(2,4,6-trimethylphenyl)-phosphinic amide, which can be made according to the procedures described in the Journal of the Chemical Society, Chemical Communications (1994), (22), 2569-70.

Suitable N-acyl imine oxygen transfer catalysts include, but are not limited to, [N(E)]-N-(phenylmethylene)acetamide, which can be made according to the procedures described in Polish Journal of Chemistry (2003), 77(5), 577-590.

Suitable thiadiazole dioxide oxygen transfer catalysts include but are not limited to, 3-methyl-4-phenyl-1,2,5-thiadiazole 1,1-dioxide, which can be made according to the procedures described in U.S. Pat. No. 5,753,599 (Column 9, Example 2).

Suitable perfluoroimine oxygen transfer catalysts include, but are not limited to, (Z)-2,2,3,3,4,4,4-heptafluoro-N-(nonafluorobutyl)butanimidoyl fluoride, which can be made according to the procedures described in Tetrahedron Letters (1994), 35(34), 6329-30.

Suitable cyclic sugar ketone oxygen transfer catalysts include, but are not limited to, 1,2:4,5-di-O-isopropylidene-D-erythro-2,3-hexodiuro-2,6-pyranose as prepared in U.S. Pat. No. 6,649,085 (Column 12, Example 1).

Preferably, the bleach catalyst comprises an iminium and/or carbonyl functional group and is typically capable of forming an oxaziridinium and/or dioxirane functional group upon acceptance of an oxygen atom, especially upon acceptance of an oxygen atom from a peroxyacid and/or salt thereof. Preferably, the bleach catalyst comprises an oxaziridinium functional group and/or is capable of forming an oxaziridinium functional group upon acceptance of an oxygen atom, especially upon acceptance of an oxygen atom from a peroxyacid and/or salt thereof. Preferably, the bleach catalyst comprises a cyclic iminium functional group, preferably wherein the cyclic moiety has a ring size of from five to eight atoms (including the nitrogen atom), preferably six atoms. Preferably, the bleach catalyst comprises an aryliminium functional group, preferably a bi-cyclic aryliminium functional group, preferably a 3,4-dihydroisoquinolinium functional group.

Typically, the imine functional group is a quaternary imine functional group and is typically capable of forming a quaternary oxaziridinium functional group upon acceptance of an oxygen atom, especially upon acceptance of an oxygen atom from a peroxyacid and/or salt thereof.

Preferably, the bleach catalyst has a chemical structure corresponding to the following chemical formula

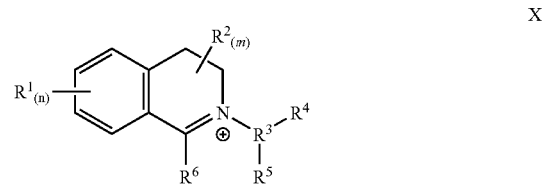

X wherein: n and m are independently from 0 to 4, preferably n and m are both 0; each $R^1$ is independently selected from a substituted or unsubstituted radical selected from the group consisting of hydrogen, alkyl, cycloalkyl, aryl, fused aryl, heterocyclic ring, fused heterocyclic ring, nitro, halo, cyano, sulphonato, alkoxy, keto, carboxylic, and carboalkoxy radicals; and any two vicinal $R^1$ substituents may combine to form a fused aryl, fused carbocyclic or fused heterocyclic ring; each $R^2$ is independently selected from a substituted or unsubstituted radical independently selected from the group consisting of hydrogen, hydroxy, alkyl, cycloalkyl, alkaryl, aryl, aralkyl, alkylenes, heterocyclic ring, alkoxys, arylcarbonyl groups, carboxyalkyl groups and amide groups; any $R^2$ may be joined together with any other of $R^2$ to form part of a common ring; any geminal R may combine to form a carbonyl; and any two $R^2$ may combine to form a substituted or unsubstituted fused unsaturated moiety; $R^3$ is a $C_1$ to $C_{20}$ substituted or unsubstituted alkyl; $R^4$ is hydrogen or the moiety $Q_t$-A, wherein: Q is a branched or unbranched alkylene, t=0 or 1 and A is an anionic group selected from the group consisting of $OSO_3^-$, $SO_3^-$, $CO_2^-$, $OCO_2^-$, $OPO_3^-$, $OPO_3H^-$ and $OPO_2^-$; $R^5$ is hydrogen or the moiety $-CR^{11}R^{12}-Y-G_b-Y_c-[(CR^9R^{10})_y-O]_k-R^8$, wherein: each Y is independently selected from the group consisting of O, S, N—H, or N—$R^8$; and each $R^8$ is independently selected from the group consisting of alkyl, aryl and heteroaryl, said moieties being substituted or unsubstituted, and whether substituted or unsubstituted said moieties having less than 21 carbons; each G is independently selected from the group consisting of CO, $SO_2$, SO, PO and $PO_2$; $R^9$ and $R^{10}$ are independently selected from the group consisting of H and $C_1$-$C_4$ alkyl; $R^{11}$ and $R^{12}$ are independently selected from the group consisting of H and alkyl, or when taken together may join to form a carbonyl; b=0 or 1; c can=0 or 1, but c must=0 if b=0; y is an integer from 1 to 6; k is an integer from 0 to 20; $R^6$ is H, or an alkyl, aryl or heteroaryl moiety; said moieties being substituted or unsubstituted; and X, if present, is a suitable charge balancing counterion, preferably X is present when $R^4$ is hydrogen, suitable X, include but are not limited to: chloride, bromide, sulphate, methosulphate, sulphonate, p-toluenesulphonate, borontetraflouride and phosphate.

In one embodiment of the present invention, the bleach catalyst has a structure corresponding to general formula below:

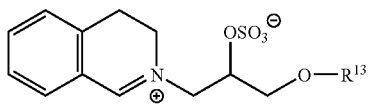

wherein $R^{13}$ is a branched alkyl group containing from three to 24 carbon atoms (including the branching carbon atoms) or a linear alkyl group containing from one to 24 carbon atoms; preferably $R^{13}$ is a branched alkyl group containing from eight to 18 carbon atoms or linear alkyl group containing from eight to eighteen carbon atoms; preferably $R^{13}$ is selected from the group consisting of 2-propylheptyl, 2-butyloctyl, 2-pentylnonyl, 2-hexyldecyl, n-dodecyl, n-tetradecyl, n-hexadecyl, n-octadecyl, iso-nonyl, iso-decyl, iso-tridecyl and iso-pentadecyl; preferably $R^{13}$ is selected from the group consisting of 2-butyloctyl, 2-pentylnonyl, 2-hexyldecyl, iso-tridecyl and iso-pentadecyl.

Oxybenzene Sulphonate and/or Oxybenzoic Bleach Activators

The composition preferably comprises (i) oxybenzene sulphonate bleach activators and/or oxybenzoic bleach activators and (ii) a source of peroxygen. Typically, the oxybenzoic acid bleach activator is in its salt form. Preferred oxybenzene sulphonate bleach activators include bleach activators having the general formula:

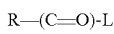

wherein R is an alkyl group, optionally branched, having, when the bleach activator is hydrophobic, from 6 to 14 carbon atoms, or from 8 to 12 carbon atoms and L is leaving group. Examples of suitable leaving groups are benzoic acid and derivatives thereof, especially salts thereof. Another especially preferred leaving group is oxybenzene sulphonate. Suitable bleach activators include dodecanoyl oxybenzene sulphonate, decanoyl oxybenzene sulphonate, a salt of decanoyl oxybenzoic acid, 3,5,5-trimethyl hexanoyloxybenzene sulphonate, nonanoylamidocaproyloxybenzene sulphonate, and nonanoyloxybenzene sulphonate (NOBS). Suitable bleach activators are also disclosed in WO 98/17767. The incorporation of these bleach activators into the composition is especially preferred when the composition comprises low levels of zeolite builder and phosphate builder. The Inventors have found that combining these bleach activators with a source of peroxygen and a bleach catalyst as described in more detail above and a lipase, especially in an under-built detergent composition (such as a detergent composition comprising low levels of zeolite-builder and phosphate-builder), improves the overall cleaning performance, improves the rubber sump hose compatibility profile, and reduces the malodor profile of the composition.

Diacyl Peroxide

In another embodiment the composition comprises: (i) a lipase; and (ii) a diacyl and/or tetraacyl peroxide species. The Inventors have found that these composition exhibit excellent rubber hose compatibility. Diacyl peroxides and also tetraacyl peroxides are known to attack rubber, such as the rubber sump hoses of automatic washing machines, and over multiple washing cycles this can lead to failure of the rubber sump hose. The Inventors have found that combining the diacyl peroxides and/or tetraacyl peroxides with lipase overcomes this problem of rubber sump hose incompatibility.

The diacyl peroxide bleaching species is preferably selected from diacyl peroxides of the general formula:

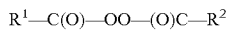

in which $R^1$ represents a $C_6$-$C_{18}$ alkyl, preferably $C_6$-$C_{12}$ alkyl group containing a linear chain of at least 5 carbon atoms and optionally containing one or more substituents (e.g. —N$^+$(CH$_3$)$_3$, —COOH or —CN) and/or one or more interrupting moieties (e.g. —CONH— or —CH=CH—) interpolated between adjacent carbon atoms of the alkyl radical, and $R^2$ represents an aliphatic group compatible with a peroxide moiety, such that $R^1$ and $R^2$ together contain a total of 8 to 30 carbon atoms. In one preferred aspect $R^1$ and $R^2$ are linear unsubstituted $C_6$-$C_{12}$ alkyl chains. Most preferably $R^1$ and $R^2$ are identical. Diacyl peroxides, in which both $R^1$ and $R^2$ are $C_6$-$C_{12}$ alkyl groups, are particularly preferred. Preferably, at least one of, most preferably only one of, the R groups ($R_1$ or $R_2$), does not contain branching or pendant rings in the alpha position, or preferably neither in the alpha nor beta positions or most preferably in none of the alpha or beta or gamma positions. In one further preferred embodiment the DAP may be asymmetric, such that preferably the hydrolysis of R1 acyl group is rapid to generate peracid, but the hydrolysis of R2 acyl group is slow.

The tetraacyl peroxide bleaching species is preferably selected from tetraacyl peroxides of the general formula:

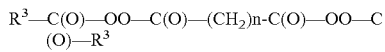

in which $R^3$ represents a $C_1$-$C_9$ alkyl, preferably $C_3$-$C_7$, group and n represents an integer from 2 to 12, preferably 4 to 10 inclusive.

Preferably, the diacyl and/or tetraacyl peroxide bleaching species is present in an amount sufficient to provide at least 0.5 ppm, more preferably at least 10 ppm, and even more preferably at least 50 ppm by weight of the wash liquor. In a preferred embodiment, the bleaching species is present in an amount sufficient to provide from about 0.5 to about 300 ppm, more preferably from about 30 to about 150 ppm by weight of the wash liquor.

Pre-Formed Peroxyacid

The pre-formed peroxyacid or salt thereof is typically either a peroxycarboxylic acid or salt thereof, or a peroxysulphonic acid or salt thereof.

The pre-formed peroxyacid or salt thereof is preferably a peroxycarboxylic acid or salt thereof, typically having a chemical structure corresponding to the following chemical formula:

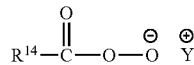

wherein: $R^{14}$ is selected from alkyl, aralkyl, cycloalkyl, aryl or heterocyclic groups; the $R^{14}$ group can be linear or branched, substituted or unsubstituted; and Y is any suitable counter-ion that achieves electric charge neutrality, preferably Y is selected from hydrogen, sodium or potassium. Preferably, $R^{14}$ is a linear or branched, substituted or unsubstituted $C_{6-9}$ alkyl. Preferably, the peroxyacid or salt thereof is selected from peroxyhexanoic acid, peroxyheptanoic acid, peroxyoctanoic acid, peroxynonanoic acid, peroxydecanoic acid, any salt thereof, or any combination thereof. Preferably, the peroxyacid or salt thereof has a melting point in the range of from 30° C. to 60° C.

The pre-formed peroxyacid or salt thereof can also be a peroxysulphonic acid or salt thereof, typically having a chemical structure corresponding to the following chemical formula:

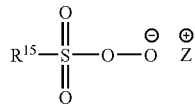

wherein: $R^{15}$ is selected from alkyl, aralkyl, cycloalkyl, aryl or heterocyclic groups; the $R^{15}$ group can be linear or branched, substituted or unsubstituted; and Z is any suitable counter-ion that achieves electric charge neutrality, preferably Z is selected from hydrogen, sodium or potassium. Preferably $R^{15}$ is a linear or branched, substituted or unsubstituted $C_{6-9}$ alkyl.

EXAMPLES

Lipase Variants Examples

Chemicals used as buffers and substrates are commercial products of at least reagent grade.
 Media and Solutions: LAS (Surfac PS™) and Zeolite A (Wessalith P™). Other ingredients used are standard laboratory reagents.
 Materials: EMPA221 from EMPA St. Gallen, Lerchfeldstrasse 5, CH-9014 St. Gallen, Switzerland Example 1

Production of Enzyme

A plasmid containing the gene encoding the lipase is constructed and transformed into a suitable host cell using standard methods of the art.

Fermentation is carried out as a fed-batch fermentation using a constant medium temperature of 34° C. and a start volume of 1.2 liter. The initial pH of the medium is set to 6.5. Once the pH has increased to 7.0 this value is maintained through addition of 10% H3PO4. The level of dissolved oxygen in the medium is controlled by varying the agitation rate and using a fixed aeration rate of 1.0 liter air per liter medium per minute. The feed addition rate is maintained at a constant level during the entire fed-batch phase.

The batch medium contained maltose syrup as carbon source, urea and yeast extract as nitrogen source and a mixture of trace metals and salts. The feed added continuously during the fed-batch phase contains maltose syrup as carbon source whereas yeast extract and urea is added in order to assure a sufficient supply of nitrogen.

Purification of the lipase may be done by use of standard methods known in the art, e.g. by filtering the fermentation supernatant and subsequent hydrophobic chromatography and anion exchange, e.g. as described in EP 0 851 913, Example 3.

Example 2

AMSA—Automated Mechanical Stress Assay—for Calculation of Relative Performance (RP)

The enzyme variants of the present application are tested using the Automatic Mechanical Stress Assay (AMSA). With the AMSA test the wash performance of a large quantity of small volume enzyme-detergent solutions can be examined. The AMSA plate has a number of slots for test solutions and a lid firmly squeezing the textile swatch to be washed against all the slot openings. During the washing time, the plate, test solutions, textile and lid are vigorously shaken to bring the test solution in contact with the textile and apply mechanical stress. For further description see WO 02/42740 especially the paragraph "Special method embodiments" at page 23-24. The containers, which contain the detergent test solution, consist of cylindrical holes (6 mm diameter, 10 mm depth) in a metal plate. The stained fabric (test material) lies on the top of the metal plate and is used as a lid and seal on the containers. Another metal plate lies on the top of the stained fabric to avoid any spillage from each container. The two metal plates together with the stained fabric are vibrated up and down at a frequency of 30 Hz with an amplitude of 2 mm.

The assay is conducted under the experimental conditions specified below:

TABLE 3

| Test solution | 0.5 g/l LAS |
| | 0.52 g/l Na2CO3 |
| | 1.07 g/l Zeolite A |
| | 0.52 g/l Tri sodium Citrate |
| Test solution volume | 160 micro l |
| pH | As is (~9.9) |
| Wash time | 20 minutes |
| Temperature | 30° C. |
| Water hardness | 15° dH |
| | Ratio of $Ca^{2+}/Mg^{2+}/NaHCO_3$: |
| | 4:1:7.5 |
| Enzyme concentration in test solution | 0.125, 0.25, 0.50, 1.0 mg enzyme protein/liter (mg ep/l) |
| Drying | Performance: After washing the textile pieces is immediately flushed in tap water and air-dried at 85 C in 5 min |
| | Odor: After washing the textile pieces is immediately flushed in tap water and dried at room temperature (20° C.) for 2 hours |
| Test material | Cream turmeric swatch as described below (EMPA221 used as cotton textile) |

Cream-turmeric swatches are prepared by mixing 5 g of turmeric (Santa Maria, Denmark) with 100 g cream (38% fat, Aria, Denmark) at 50° C., the mixture is left at this temperature for about 20 minutes and filtered (50° C.) to remove any undissolved particles. The mixture is cooled to 20° C.) woven cotton swatches, EMPA221, are immersed in the cream-turmeric mixture and afterwards allowed to dry at room temperature over night and frozen until use. The preparation of cream-turmeric swatches is disclosed in the patent application PA 2005 00775, filed 27 May 2005.

The performance of the enzyme variant is measured as the brightness of the colour of the textile samples washed with that specific enzyme variant. Brightness can also be expressed as the intensity of the light reflected from the textile sample when luminated with white light. When the textile is stained the intensity of the reflected light is lower, than that of a clean textile. Therefore the intensity of the reflected light can be used to measure wash performance of an enzyme variant.

Color measurements are made with a professional flatbed scanner (PFU DL2400pro), which is used to capture an image of the washed textile samples. The scans are made with a resolution of 200 dpi and with an output color depth of 24 bits. In order to get accurate results, the scanner is frequently calibrated with a Kodak reflective IT8 target.

To extract a value for the light intensity from the scanned images, a special designed software application is used (Novozymes Color Vector Analyzer). The program retrieves the 24 bit pixel values from the image and converts them into values for red, green and blue (RGB). The intensity value (Int) is calculated by adding the RGB values together as vectors and then taking the length of the resulting vector:

$$Int=\sqrt{r^2+g^2+b^2}.$$

The wash performance (P) of the variants is calculated in accordance with the formula:

$$P=Int(v)-Int(r) \text{ where}$$

Int(v) is the light intensity value of textile surface washed with tested enzyme and Int(r) is the light intensity value of textile surface washed without the tested enzyme.

A relative performance score is given as the result of the AMSA wash in accordance with the definition: Relative Performance scores (RP) are summing up the performances (P) of the tested enzyme variants against the reference enzyme: RP=P(test enzyme)/P(reference enzyme). RPavg indicates the average relative performance compared to the reference enzyme at all four enzyme concentrations (0.125, 0.25, 0.5, 1.0 mg ep/l)

$$RPavg=avg(RP(0.125), RP(0.25)\ RP(0.5), RP(1.0))$$

A variant is considered to exhibit improved wash performance, if it performs better than the reference. In the context of the present invention the reference enzyme is the lipase of SEQ ID NO:2 with the substitutions T231R+N233R.

Example 3

GC—Gas Chromatograph—for Calculation of Risk Factor

The butyric acid release from the lipase washed swatches are measured by Solid Phase Micro Extraction Gas Chromatography (SPME-GC) using the following method. Four textile pieces (5 mm in diameter), washed in the specified solution in Table 3 containing 1 mg/l lipase, are transferred to a Gas Chromatograph (GC) vial. The samples are analysed on a Varian 3800 GC equipped with a Stabilwax-DA w/Integra-Guard column (30 m, 0.32 mm ID and 0.25 micro-m df) and a Carboxen PDMS SPME fibre (75 micro-m). Each sample is preincubated for 10 min at 40° C. followed by 20 min sampling with the SPME fibre in the head-space over the textile pieces. The sample is subsequently injected onto the column (injector temperature=250° C.). Column flow=2 ml Helium/min. Column oven temperature gradient: 0 min=40° C., 2 min=40° C., 22 min=240° C., 32 min=240° C. The butyric acid is detected by FID detection and the amount of butyric acid is calculated based on a butyric acid standard curve.

The Risk Performance Odour, R, of a lipase variant is the ratio between the amount of released butyric acid from the lipase variant washed swatch and the amount of released butyric acid from a swatch washed with the lipase of SEQ ID NO: 2 with the substitutions T231R+N233R (reference enzyme), after both values have been corrected for the amount of released butyric acid from a non-lipase washed swatch. The risk (R) of the variants is calculated in accordance with the below formula:

Odour=measured in micro g butyric acid developed at 1 mg enzyme protein/l corrected for blank $$\alpha_{test\ enzyme}=Odour_{test\ enzyme}-Blank$$

$$\alpha_{reference\ enzyme}=Odour_{reference\ enzyme}-Blank$$

$$R=\alpha_{test\ enzyme}/\alpha_{reference\ enzyme}$$

A variant is considered to exhibit reduced odor compared to the reference, if the R factor is lower than 1.

Example 4

Activity (LU) Relative to Absorbance at 280 nm

The activity of a lipase relative to the absorbance at 280 nm is determined by the following assay

LU/A280:

The activity of the lipase is determined as described above in the section Lipase activity. The absorbance of the lipase at 280 nm is measured (A280) and the ratio LU/A280 is calculated. The relative LU/A280 is calculated as the LU/A280 of the variant divided by the LU/A280 of a reference enzyme. In the context of the present invention the reference enzyme is the lipase of SEQ ID NO:2 with the substitutions T231R+N233R.

Example 5

BR—Benefit Risk

The Benefit Risk factor describing the performance compared to the reduced risk for odour smell is thus defined as: BR=$RP_{avg}$/R A variant is considered to exhibit improved wash performance and reduced odor, if the BR factor is higher than 1.

Applying the above methods the following results are obtained:

TABLE 4

| Variant | Mutations in SEQ ID NO: 2 | Average RP ($RP_{avg}$) | BR | LU/A280 |
|---|---|---|---|---|
| 1 | I202G + T231R + N233R | 0.84 | 1.41 | not determined |
| 2 | I86V + L227G + T231R + N233R + P256K | 1.08 | 1.52 | 1700 |
| 3 | Q4V + S58N + V60S + T231R + N233R | 0.87 | 1.73 | 1950 |
| 4 | S58N + V60S + I90R + T231R + N233R | 1.06 | 1.27 | 2250 |
| 5 | I255Y + T231R + N233R | 1.19 | 1.17 | 3600 |
| 6 | I90A + T231R + N233R + I255V | 1.13 | 1.14 | 2700 |

TABLE 4-continued

| Variant | Mutations in SEQ ID NO: 2 | Average RP ($RP_{avg}$) | BR | LU/A280 |
|---|---|---|---|---|
| Reference | T231R + N233R | 1.00 | 1.00 | 3650 |
| 7 | G91A + E99K + T231R + N233R + Q249R + 270H + 271T + 272P + 273S + 274S + 275G + 276R + 277G + 278G + 279H + 280R | 0.43 | not determined | 850 |
| 8 | G91A + E99K + T231R, N233R + Q249R + 270H + 271T + 272P + 273S + 274S + 275G + 276R + 277G + 278G | 0.13 | not determined | 500 |

The reference lipase and variants 7 and 8 in Table 4 are described in WO 2000/060063.

Example 6

BR—Benefit Risk

The Benefit Risk was measured for the variants listed in Table 5. The Benefit Risk factor was measured in the same way as described in Example 5 and it was found to be above 1 for all the listed variants.

TABLE 5

| Variant | Mutations in SEQ ID NO: 2 |
|---|---|
| Reference | T231R + N233R |
| 9 | L97V + T231R + N233R |
| 10 | A150G + T231R + N233R |
| 11 | I90R + T231R + N233R |
| 12 | I202V + T231R + N233R |
| 13 | L227G + T231R + N233R + P256K |
| 14 | I90A + T231R + N233R |
| 15 | T231R + N233R + I255P |
| 16 | I90V + I255V + T231R + N233R |
| 17 | F211L + L227G + T231R + N233R + I255L + P256K |
| 18 | S58N + V60S + T231R + N233R + Q249L |
| 19 | S58N + V60S + T231R + N233R + Q249I |
| 20 | A150G + L227G + T231R + N233R + P256K |
| 21 | K46L + S58N + V60S + T231R + N233R + Q249L + D254I |
| 22 | Q4L + E43T + K46I + S58N + V60S + T231R + N233R + Q249L + D254I |
| 23 | Q4L + S58N + V60S + T231R + N233R + Q249L + D254I |
| 24 | K46I + S58N + V60S + T231R + N233R + Q249L + D254L |
| 25 | K46L + S58N + V60S + K223I + T231R + N233R + D254I |
| 26 | E43T + K46I + S58N + V60S + T231R + N233R + Q249L + D254I |
| 27 | S58N + V60S + I86V + A150G + L227G + T231R + N233R + P256K |
| 28 | K24R + K46R + K74R + I86V + K98R + K127R + D137K + A150G + K223R + T231R + N233R |
| 29 | S58A + V60A + I86V + T231R + N233R |
| 30 | K24R + K46R + S58N + V60S + K74R + I86V + K98R + K127R + D137K + K223R + T231R + N233R |
| 31 | S58A + V60A + I86V + A150G + T231R + N233R |
| 32 | S58N + V60V + D62G + T231R + N233R |
| 33 | Q4V + S58N + V60S + I86V + T231R + N233R + Q249L |
| 34 | Q4V + S58N + V60S + I86V + A150G + T231R + N233R + I255V |
| 35 | Q4V + S58N + V60S + I90A + A150G + T231R + N233R + I255V |
| 36 | Y53A + S58N + V60S + T231R + N233R + P256L |
| 37 | I202L + T231R + N233R + I255A |
| 38 | S58A + V60S + I86V + A150G + L227G + T231R + N233R + P256K |
| 39 | D27R + S58N + V60S + I86V + A150G + L227G + T231R + N233R + P256K |
| 40 | V60K + I86V + A150G + L227G + T231R + N233R + P256K |
| 41 | Q4V + S58A + V60S + S83T + I86V + A150G + E210K + L227G + T231R + N233R + P256K |
| 42 | Q4V + V60K + S83T + I86V + A150G + L227G + T231R + N233R + P256K |
| 43 | D27R + V60K + I86V + A150G + L227G + T231R + N233R + P256K |
| 44 | Q4N + L6S + S58N + V60S + I86V + A150G + L227G + T231R + N233R + P256K |
| 45 | E1N + V60K + I86V + A150G + L227G + T231R + N233R + P256K |
| 46 | V60K + I86V + A150G + K223N + G225S + T231R + N233R + P256K |
| 47 | E210V + T231R + N233R + Q249R |
| 48 | S58N + V60S + E210V + T231R + N233R + Q249R |
| 49 | Q4V + V60K + I90R + T231R + N233R + I255V |
| 50 | Q4V + V60K + A150G + T231R + N233R |
| 51 | V60K + S83T + T231R + N233R |
| 52 | V60K + A150G + T231R + N233R + I255V |
| 53 | T231R + N233G + D234G |
| 54 | S58N + V60S + I86V + A150G + E210K + L227G + T231R + N233R + Q249R + P256K |
| 55 | S58N + V60S + I86V + A150G + E210K + L227G + T231R + N233R + I255A + P256K |

TABLE 5-continued

| Variant | Mutations in SEQ ID NO: 2 |
|---|---|
| 56 | S58N + V60S + I86V + A150G + G156R + E210K + L227G + T231R + N233R + I255A + P256K |
| 57 | S58T + V60K + I86V + N94K + A150G + E210V + L227G + T231R + N233R + P256K |
| 58 | S58T + V60K + I86V + D102A + A150G + L227G + T231R + N233R + P256K |
| 59 | S58T + V60K + I86V + D102A + A150G + E210V + L227G + T231R + N233R + P256K |
| 60 | S58T + V60K + S83T + I86V + N94K + A150G + E210V + L227G + T231R + N233R + P256K |
| 61 | S58A + V60S + I86V + T143S + A150G + L227G + T231R + N233R + P256K |
| 62 | G91S + D96V + D254R |
| 63 | V60L + G91M + T231W + Q249L |
| 64 | T37A + D96A + T231R + N233R + Q249G |
| 65 | E56G + E87D + T231R + N233R + D254A |
| 66 | E210K + T231R + N233R |
| 67 | D27H + E87Q + D96N + T231R + N233R + D254V |
| 68 | F181L + E210V + T231R + N233R |
| 69 | D27N + D96G + T231R + N233R |
| 70 | D96N + T231R + N233R |
| 71 | T231R + N233I + D234G |
| 72 | S58K + V60L + E210V + Q249R |
| 73 | S58H + V60L + E210V + Q249R |
| 74 | Q4V + F55V + I86V + T231R + N233R + I255V |
| 75 | Q4V + S58T + V60K + T199L + N200A + E210K + T231R + N233R + I255A + P256K |
| 76 | Q4V + D27N + V60K + T231R + N233R |
| 77 | I90F + I202P + T231R + N233R + I255L |
| 78 | S58N + V60S + D158N + T231R + N233R |
| 79 | S58N + V60S + S115K + T231R + N233R |
| 80 | S58N + V60S + L147M + A150G + F211L + T231R + N233R |
| 81 | V60K + A150G + T231R + N233R |
| 82 | I90V + L227G + T231R + N233R + P256K |
| 83 | T231R + N233R + I255S |
| 84 | I86G + T231R + N233R |
| 85 | V60K + I202V + E210K + T231R + N233R + I255A + P256K |
| 86 | I90G + I202L + T231R + N233R + I255S |
| 87 | S58G + V60G + T231R + N233R |

The reference lipase is described in WO 2000/060063.

Bleach Catalyst Examples

Example 6

Preparation of Sulphuric Acid mono-[2-(3,4-dihydro-isoquinolin-2-yl)-1-(2-ethylhexyloxymethyl)-ethyl]-ester, Internal Salt Preparation of 2-ethylhexyl glycidyl ether: To a flame dried, 500 mL round bottomed flask equipped with an addition funnel charged with epichlorohydrin (15.62 g, 0.17 moles), is added 2-ethylhexanol (16.5 g, 0.127 moles) and stannic chloride (0.20 g, 0.001 moles). The reaction is kept under an argon atmosphere and warmed to 90° C. using an oil bath. Epichlorohydrin is dripped into the stirring solution over 60 minutes followed by stirring at 90° C. for 18 hours. The reaction is fitted with a vacuum distillation head and 1-chloro-3-(2-ethyl-hexyloxy)-propan-2-ol is distilled under 0.2 mm Hg. The 1-chloro-3-(2-ethyl-hexyloxy)-propan-2-ol (4.46 g, 0.020 moles) is dissolved in tetrahydrofuran (50 mL) and stirred at room temperature under an argon atmosphere. To the stirring solution is added potassium tert-butoxide (2.52 g, 0.022 moles) and the suspension is stirred at room temperature for 18 hours. The reaction is then evaporated to dryness, residue dissolved in hexanes and washed with water (100 mL). The hexanes phase is separated, dried with Na$_2$SO$_4$, filtered and evaporated to dryness to yield the crude 2-ethylhexyl glycidyl ether, which can be further purified by vacuum distillation.

Preparation of Sulphuric acid mono-[2-(3,4-dihydro-isoquinolin-2-yl)-1-(2-ethylhexyloxymethyl)-ethyl] ester, internal salt: To a flame dried 250 mL three neck round bottomed flask, equipped with a condenser, dry argon inlet, magnetic stir bar, thermometer, and heating bath is added 3,4-dihydroisoquinoline (0.40 mol.; prepared as described in Example I of U.S. Pat. No. 5,576,282), 2-ethylhexyl glycidyl ether (0.38 mol, prepared as described above), SO$_3$-DMF complex (0.38 mol), and acetonitrile (500 mL). The reaction is warmed to 80° C. and stirred at temperature for 72 hours. The reaction is cooled to room temperature, evaporated to dryness and the residue recrystallized from ethyl acetate and/or ethanol to yield the desired product. The solvent acetonitrile may be replaced with other solvents, including but not limited to, 1,2-dichloroethane.

Example 7

Preparation of Sulphuric Acid mono-[2-(3,4-dihydro-isoquinolin-2-yl)-1-(2-butyl-octyloxymethyl)-ethyl]ester, Internal Salt The desired product is prepared according to Example 1 but substituting 2-butyloctanol for 2-hexyloctanol.

Composition Example

The lipase incorporated in the compositions below is the lipase variant 1 to 5 described in example 5 Table 4, and combinations thereof.

Example 8

Laundry Detergent Compositions

The following laundry detergent compositions A, B, C and D are suitable for use in the present invention. Typically, these compositions are dosed into water at a concentration of from 80 g/l to 120 g/l during the laundering process.

| Ingredient | A | B | C | D |
|---|---|---|---|---|
| Bleach catalyst made according to example 6 or 7 | 0.1 wt % | 0.05 wt % | 0.03 wt % | 0.05 wt % |
| Lipase (9 mg/g acive) | 0.15 wt % | 0.2 wt % | 0.3 wt % | 0.2 wt % |
| Sodium linear $C_{12-13}$ alkyl benzenesulphonate (LAS) | 9.0 wt % | 8 wt % | 7.5 wt % | 7.0 wt % |
| Tallow alkyl sulphate (TAS) | 1.0 wt % | 1.0 wt % | | |
| $C_{14-15}$ alkyl ethoxylated alcohol having an average degree of ethoxylation of 7 (AE7) | 2.5 wt % | | | |
| $C_{14-15}$ alkyl ethoxylated alcohol sulphate having an average degree of ethoxylation of 3 ($AE_3S$) | | 4 wt % | 3.0 wt % | 2.5 wt % |
| Mono-$C_{12-14}$ alkyl mono-hydroxyethyl di-methyl quaternary ammonium chloride | 1.5 wt % | 1.0 wt % | | |
| Zeolite 4A | 15 wt % | 12.5 wt % | | |
| Citric Acid | 3.0 wt % | 2.0 wt % | 3.0 wt % | 3.0 wt % |
| Sodium Percarbonate | 20 wt % | 15 wt % | 17.5 wt % | 14 wt % |
| TAED (tetraacetylethylenediamine) | 2.5 wt % | 3 wt % | 2.3 wt % | 1.6 wt % |
| NOBS (nonanoyloxybenzene sulphonate) | 0.0% | 1.0 wt % | 0.0 wt % | 1.5 wt % |
| Sodium carbonate | 20 wt % | 25 wt % | 20 wt % | 25 wt % |
| Polymeric carboxylate | 2.0 wt % | 1.5 wt % | 3.0 wt % | 2.5 wt % |
| A compound having the following general structure: bis$((C_2H_5O)(C_2H_4O)n)(CH_3)$—$N^+$—$C_xH_{2x}$—$N^+$—$(CH_3)$-bis$((C_2H_5O)(C_2H_4O)n)$, wherein n = from 20 to 30, and x = from 3 to 8, or sulphated or sulphonated variants thereof | 1.0 wt % | 0.5 wt % | 0.75 t % | 1.0 wt % |
| Carboxymethyl cellulose | | | 1.5 wt % | 1.0 wt % |
| Other enzymes | 1.0 wt % | 0.5 wt % | 0.75 wt % | 0.5 wt % |
| Ethylene diamine disuccinic acid | 0.5 wt % | 0.1 wt % | 0.2 wt % | 0.25 wt % |
| Magnesium sulphate | 0.75 wt % | 0.5 wt % | 1.0 wt % | 0.5 wt % |
| Hydroxyethane di(methylene phosphonic acid) | 0.5 wt % | 0.25 wt % | 0.2 wt % | 0.4 wt % |
| Fluorescent whitening agent | 0.2 wt % | 0.1 wt % | 0.15 wt % | 0.25 wt % |
| Silicone suds suppressing agent | 0.1 wt % | 0.05 wt % | 0.1 wt % | 0.1 wt % |
| Soap | 0.5 wt % | 0.25 wt % | 0.0 wt % | 0.3 wt % |
| Photobleach | 0.01 wt % | 0.0001 wt % | 0.0005 wt % | 0.0015 wt % |
| Perfume | 1.0 wt % | 0.5 wt % | 0.75 wt % | 0.5 wt % |
| Sodium sulphate | 13 wt % | 15 wt % | 30 wt % | 30 wt % |
| Water and miscellaneous | to 100 wt % | to 100 wt % | to 100 wt % | to 100 wt % |

The following laundry detergent compositions E, F, G and H are suitable for use in the present invention. Typically, these compositions are dosed into water at a concentration of from 80 g/l to 120 g/l during the laundering process.

| Ingredient | E | F | G | H |
|---|---|---|---|---|
| Bleach catalyst made according to example 6 or 7 | | | 0.01 wt % | 0.05 wt % |
| Diacyl peroxide | 2 wt % | 1 wt % | 0.5 wt % | 1 wt % |
| Lipase (9 mg/g active enzyme) | 0.5 wt % | 0.3 wt % | 0.2 wt % | 0.1 wt % |
| Sodium linear $C_{12-13}$ alkyl benzenesulphonate (LAS) | 8.0 wt % | 5.0 wt % | 7.5 wt % | 7.0 wt % |
| $C_{14-15}$ alkyl ethoxylated alcohol sulphate having an average degree of ethoxylation of 3 ($AE_3S$) | 5.0 wt % | 2.5 wt % | 3.5 wt % | 6.0 wt % |
| Citric Acid | 3.0 wt % | 2.0 wt % | 5.0 wt % | 2.5 wt % |
| Sodium carbonate | 20 wt % | 25 wt % | 22.5 wt % | 25 wt % |
| Polymeric carboxylate | 2.0 wt % | 3.5 wt % | 3.5 wt % | 2.5 wt % |
| A compound having the following general structure: bis$((C_2H_5O)(C_2H_4O)n)(CH_3)$—$N^+$—$C_xH_{2x}$—$N^+$—$(CH_3)$-bis$((C_2H_5O)(C_2H_4O)n)$, wherein n = from 20 to 30, and x = from 3 to | 1.0 wt % | 0.5 wt % | 0.75 wt % | 1.0 wt % |

| Ingredient | E | F | G | H |
|---|---|---|---|---|
| 8, or sulphated or sulphonated variants thereof | | | | |
| Sodium Percarbonate | 0 wt % | 15 wt % | 17.5 wt % | 14 wt % |
| TAED (tetraacetylethylenediamine) | 0 wt % | 3 wt % | 2.3 wt % | 1.6 wt % |
| Carboxymethyl cellulose | 0.5 wt % | 1.0 wt % | 1.5 wt % | 1.0 wt % |
| Other Enzymes | 1.0 wt % | 0.5 wt % | 0.2 wt % | 0.5 wt % |
| Ethylene diamine disuccinic acid | 0.05 wt % | 0.1 wt % | 0.2 wt % | 0.15 wt % |
| Magnesium sulphate | 0.35 wt % | 0.1 wt % | 1.0 wt % | 0.25 wt % |
| Hydroxyethane di(methylene phosphonic acid) | 0.1 wt % | 0.25 wt % | 0.2 wt % | 0.5 wt % |
| Fluorescent whitening agent | 0.2 wt % | 0.1 wt % | 0.15 wt % | 0.25 wt % |
| Silicone suds suppressing agent | 0.1 wt % | 0.05 wt % | 0.1 wt % | 0.2 wt % |
| Soap | 0.5 wt % | 0.25 wt % | 1.0 wt % | 0.5 wt % |
| Photobleach | 0.01 wt % | 0.0001 wt % | 0.0005 wt % | 0.0015 wt % |
| Perfume | 1.0 wt % | 0.5 wt % | 0.75 wt % | 0.5 wt % |
| Sodium sulphate | 45 wt % | 30 wt % | 20 wt % | 22 wt % |
| Water and miscellaneous | to 100 wt % | to 100 wt % | to 100 wt % | to 100 wt % |

The following laundry detergent compositions I, J, K and L are suitable for use in the present invention. Typically, these compositions are dosed into water at a concentration of from 20 g/l to 60 g/l during the laundering process.

| Ingredient | I | J | K | L |
|---|---|---|---|---|
| Bleach catalyst made according to example 6 or 7 | 0.15 wt % | 0.10 wt % | 0.1 wt % | 0.15 wt % |
| Diacyl peroxide | | 1 wt % | 0.5 wt % | |
| Lipase | 0.5 wt % | 0.3 wt % | 0.1 wt % | 0.2 wt % |
| Sodium linear $C_{12-13}$ alkyl benzenesulphonate (LAS) | 15 wt % | 17.5 wt % | 20 wt % | 10.0 wt % |
| $C_{14-15}$ alkyl ethoxylated alcohol sulphate having an average degree of ethoxylation of 3 ($AE_3S$) | 7.0 wt % | 7.5 wt % | 5.0 wt % | 5.0 wt % |
| Citric Acid | 7.0 wt % | 5.0 wt % | 7.5 wt % | 3.0 wt % |
| Sodium Percarbonate | 20 wt % | 15 wt % | 0 wt % | 14 wt % |
| TAED (tetraacetylethylenediamine) | 2.5 wt % | 3 wt % | 0 wt % | 1.6 wt % |
| NOBS (nonanoyloxybenzene sulphonate) | 0.0 wt % | 2.0 wt % | 0.0 wt % | 0 wt % |
| Sodium carbonate | 22.5 wt % | 25 wt % | 20 wt % | 10 wt % |
| Polymeric carboxylate | 7.0 wt % | 7.5 wt % | 5.0 wt % | 3.0 wt % |
| A compound having the following general structure: bis(($C_2H_5O$)($C_2H_4O$)n)($CH_3$)—$N^+$—$C_xH_{2x}$—$N^+$—($CH_3$)-bis(($C_2H_5O$)($C_2H_4O$)n), wherein n = from 20 to 30, and x = from 3 to 8, or sulphated or sulphonated variants thereof | 2.5 wt % | 1.5 wt % | 3.0 wt % | 1.0 wt % |
| Carboxymethyl cellulose | 2.5 wt % | 3.0 wt % | 1.5 wt % | 1.0 wt % |
| Other Enzymes | 2.5 wt % | 1.5 wt % | 3.0 wt % | 0.75 wt % |
| Ethylene diamine disuccinic acid | 0.25 wt % | 0.1 wt % | 0.5 wt % | 0.15 wt % |
| Hydroxyethane di(methylene phosphonic acid) | 0.5 wt % | 0.75 wt % | 0.25 wt % | 0.2 wt % |
| Fluorescent whitening agent | 0.5 wt % | 0.75 wt % | 0.25 wt % | 0.15 wt % |
| Silicone suds suppressing agent | 0.05 wt % | 0.10 wt % | 0.02 wt % | 0.02 wt % |
| Photobleach | 0.025 wt % | 0.050 wt % | 0.02 wt % | 0.0015 wt % |
| Water, filler (including sodium sulphate) and miscellaneous | to 100 wt % | to 100 wt % | to 100 wt % | to 100 wt % |

Bleaching detergent compositions having the form of granular laundry detergents are exemplified by the following formulations. Any of the below compositions is used to launder fabrics at a concentration of 600-10000 ppm in water, with typical median conditions of 2500 ppm, 25° C., and a 25:1 water:cloth ratio. The typical pH is about 10 but can be can be adjusted by altering the proportion of acid to Na-salt form of alkylbenzenesulfonate.

|  | M | N | O | P | Q | R |
|---|---|---|---|---|---|---|
| Linear alkylbenzenesulfonate | 20 | 22 | 20 | 15 | 20 | 20 |
| $C_{12}$ Dimethylhydroxyethyl ammonium chloride | 0.7 | 1 | 0.0 | 0.6 | 0.0 | 0.7 |
| AE3S | 0.9 | 0.0 | 0.9 | 0.0 | 0.0 | 0.9 |
| AE7 | 0.0 | 0.5 | 0.0 | 1 | 3 | 1 |
| sodium tripolyphosphate | 23 | 30 | 23 | 17 | 12 | 23 |
| Zeolite A | 0.0 | 0.0 | 0.0 | 0.0 | 10 | 0.0 |
| 1.6R Silicate | 7 | 7 | 7 | 7 | 7 | 7 |
| Sodium Carbonate | 15 | 14 | 15 | 18 | 15 | 15 |
| Polyacrylate MW 4500 | 1 | 0.0 | 1 | 1 | 1.5 | 1 |
| Carboxy Methyl Cellulose | 1 | 1 | 1 | 1 | 1 | 1 |
| Savinase 32.89 mg/g | 0.1 | 0.07 | 0.1 | 0.1 | 0.1 | 0.1 |
| Natalase 8.65 mg/g | 0.1 | 0.1 | 0.1 | 0.0 | 0.1 | 0.1 |
| Lipase 18 mg/g* | 0.03 | 0.07 | 0.3 | 0.1 | 0.07 | 0.1 |
| Tinopal AMS (ex. Ciba) | 0.06 | 0.0 | 0.06 | 0.18 | 0.06 | 0.06 |
| Tinopal CBS-X (ex. Ciba) | 0.1 | 0.06 | 0.1 | 0.0 | 0.1 | 0.1 |
| Diethylenetriamine pentacetic acid | 0.6 | 0.3 | 0.6 | 0.25 | 0.6 | 0.6 |
| $MgSO_4$ | 1 | 1 | 1 | 0.5 | 1 | 1 |
| Sodium Percarbonate | 0.0 | 5.2 | 0.1 | 0.0 | 0.0 | 0.0 |
| Photobleach | 0.0030 | 0.0015 | 0.0015 | 0.0020 | 0.0045 | 0.0010 |
| Sodium Perborate Monohydrate | 4.4 | 0.0 | 3.85 | 2.09 | 0.78 | 3.63 |
| NOBS | 1.9 | 0.0 | 1.66 | 0.0 | 0.33 | 0.75 |
| TAED | 0.58 | 1.2 | 0.51 | 0.0 | 0.015 | 0.28 |
| Organic Catalyst** | 0.0185 | 0.0185 | 0.0162 | 0 | 0.0111 | 0.0074 |
| Diacyl peroxide*** |  | 0.5 |  | 1 |  |  |
| Sulfate/Moisture | Balance to 100% | Balance to 100% | Balance to 100% | Balance to 100% | Balance to 100% | Balance to 100% |

*Lipase variant 1 to 5 described in example 5 Table 4, and combinations thereof.
**Organic catalyst prepared according to Examples 6 or 7 or mixtures thereof.
***Diacyl peroxide is preferably dinonanoylperoxide.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention. All documents cited are, in relevant part, incorporated herein by reference, the citation of any document is not to be construed as an admission that it is prior art with respect to the present invention.

The invention claimed is:

1. A composition comprising:
   a) a variant of a parent lipase, said parent lipase having a sequence corresponding to SEQ ID NO:2, said variant, when compared to said parent, comprising a total of at least three substitutions, at least two of said substitutions being in Region I, said substitutions being selected from one or more of the following groups of substitutions:
   (i) at least two substitutions in Region I, said substitutions in Region I comprising substitutions in the positions corresponding to the positions 231 and 233 of SEQ ID NO:2,
   (ii) at least one substitution in Region II,
   (iii) at least one substitution in Region III, and/or
   (iv) at least one substitution in Region IV; and
   b) a bleach catalyst that is capable of accepting an oxygen atom from a peroxyacid and transferring the oxygen atom to an oxidizeable substrate.

2. A detergent composition according to claim 1 wherein said substitutions at positions 231 and 233 are substituted with an R.

3. A detergent composition according to claim 2, wherein said variant comprises a substitution in the position corresponding to position 4 of SEQ ID NO:2.

4. A detergent composition according to claim 3, wherein said variant corresponding to position 4 of SEQ ID NO:2 is V.

5. A detergent composition according to claim 1, wherein said variant comprises a substitution in the position corresponding to position 227 of SEQ ID NO:2.

6. A detergent composition according to claim 5, wherein said variant corresponding to position 227 of SEQ ID NO:2 is G.

7. A detergent composition according to claim 1, wherein said at least one substitution in Region II comprises a substitution selected from the group consisting of substitutions in positions corresponding to the positions 202, 211, 255 and 256.

8. A detergent composition according to claim 7, wherein said at least one substitution in Region II comprises a substitution selected from the group consisting of X202G, X211L, X255Y/V and X256K.

9. A detergent composition according to claim 1, wherein said at least one substitution in Region II comprises a substitution in the position corresponding to the position 210.

10. A detergent composition according to claim 9, wherein said substitution corresponding to position 210 comprises X210HK.

11. A detergent composition according to claim 1, wherein said at least one substitution in Region III comprises a substitution selected from the group consisting of substitutions in positions corresponding to the positions 86 and 90.

12. A detergent composition according to claim 11, wherein said at least one substitution in Region III comprises a substitution selected from the group consisting of X86V and X90A/R.

13. A detergent composition according to claim 1, wherein said at least one substitution in Region III comprises a substitution in the position corresponding to the position 83.

14. A detergent composition according to claim 13, wherein said substitution corresponding to position 83 comprises X83T.

15. A detergent composition according to claim 1, wherein said at least one substitution in Region IV comprises a substitution selected from the group consisting of substitutions in positions corresponding to the positions 27, 58 and 60.

16. A detergent composition according to claim 15, wherein said at least one substitution in Region IV comprises a substitution selected from the group consisting of X27R, X58N/A/G/P/T and X60S/G/N/R/K/A/L.

17. A detergent composition according to claim 1, comprising at least two substitutions in Region IV corresponding to the positions 27, 58 and 60.

18. A detergent composition according to claim 17, comprising at least two substitutions in Region IV selected from the group consisting of X27R, X58N/A/G/P/T and X60S/G/N/R/K/A/L.

19. A detergent composition according to claim 1, wherein said variant comprises at least one substitution outside the defined Regions I to IV.

20. A detergent composition according to claim 19, wherein said at least one substitution outside the defined Regions I to IV is selected from the group consisting of substitutions in positions corresponding to position 81, 147, 150 and 249.

21. A detergent composition according to claim 19, wherein said at least one substitution outside the defined Regions I to IV is selected from the group consisting of X81Q/E, X147M/Y, X150G and X249R/I/L.

22. A detergent composition according to claim 1 wherein the parent lipase is identical to SEQ ID NO: 2 and said variant comprises one of the following groups of substitutions:
   a) T231R+N233R+I255Y
   b) I202G+T231R+N233R
   c) I86V+L227G+T231R+N233R+P256K
   d) Q4V+S58N+V60S+T231R+N233R
   e) S58N+V60S+I90R+T231R+N233R
   f) I90A+T231R+N233R+I255V g) S58N+V60S+I86V+A150G+L227G+T231R+N233R+ P256K h) S58N+V60S+L147M+F211L+T231R+N233R i) Q4V+S58A+V60S+S83T+I86V+A150G+E210K+ L227G +T231R+N233R+P256K j) S58N+V60S+I86V+A150G+L227G+T231R+N233R+ P256K.

23. A detergent composition according to claim 1 wherein the parent lipase is identical to SEQ ID NO: 2 and said variant comprises one of the following groups of substitutions:

a) Q4V+S58A+V60S+S83T+I86V+A150G+E210K+ L227G +T231R+N233R+P256K b) S58N+V60S+I86V+A150G+L227G+T231R+N233R+ P256K.

24. A detergent composition according to claim 1 wherein the lipase variant is characterized in that the Benefit Risk, when measured as given in the specification, is larger than 1.

25. The detergent composition of claim 1 comprising:

a) polypeptide having lipase activity and which further has a Average Relative Performance of at least 0.8 and a Benefit Risk of at least 1.1 at the test conditions given in the specification; and b) a bleach catalyst that is capable of accepting an oxygen atom from a peroxyacid and transferring the oxygen atom to an oxidizeable substrate.

26. A composition according to claim 25, wherein the bleach catalyst comprises a moiety selected from the group consisting of iminium cations and polyions; iminium zwitterions; modified amines; modified amine oxides; N-sulphonyl imines; N-phosphonyl imines; N-acyl imines; thiadiazole dioxides; perfluoroimines; cyclic sugar ketones and mixtures thereof.

27. A composition according to claim 25, wherein the bleach catalyst comprises an iminium and/or a carbonyl functional group.

28. A composition according to claim 1, wherein the bleach catalyst comprises an oxaziridinium and/or a dioxirane functional group, and/or is capable of forming an oxaziridinium and/or a dioxirane functional group upon acceptance of an oxygen atom.

29. A composition according to claim 1, wherein the bleach catalyst has a chemical structure corresponding to the chemical formula:

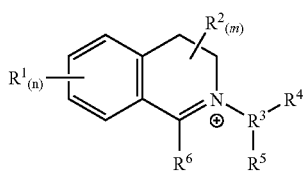

wherein: n and m are independently from 0 to 4; each $R^1$ is independently selected from a substituted or unsubstituted radical selected from the group consisting of hydrogen, alkyl, cycloalkyl, aryl, fused aryl, heterocyclic ring, fused heterocyclic ring, nitro, halo, cyano, sulphonato, alkoxy, keto, carboxylic, and carboalkoxy radicals, and any two vicinal $R^1$ substituents may combine to form a fused aryl, fused carbocyclic or fused heterocyclic ring; each $R^2$ is independently selected from a substituted or unsubstituted radical independently selected from the group consisting of hydrogen, hydroxy, alkyl, cycloalkyl, alkaryl, aryl, aralkyl, alkylenes, heterocyclic ring, alkoxy, arylcarbonyl groups, carboxyalkyl groups and amide groups; any $R^2$ may be joined together with any other of $R^2$ to form part of a common ring; any geminal $R^2$ may combine to form a carbonyl; and wherein any two $R^2$ may combine to form a substituted or unsubstituted fused unsaturated moiety; $R^3$ is a $C_1$ to $C_{20}$ substituted or unsubstituted alkyl; $R^4$ is hydrogen or the moiety $Q_t$-A, wherein: Q is a branched or unbranched alkylene, t=0 or 1, and A is an anionic group selected from the group consisting of $OSO_3^-$, $SO_3^-$, $CO_2^-$, $OCO_2^-$, $OPO_3^{2-}$, $OPO_3H^-$ and $OPO_2^-$; $R^5$ is hydrogen or the moiety $-CR^{11}R^{12}-Y-G_b-Y_c-[(CR^9R^{10})_y-O]_k-R^8$, wherein: each Y is independently selected from the group consisting of O, S, N—H, or N—$R^8$; and each $R^8$ is independently selected from the group consisting of alkyl, aryl and heteroaryl, said moieties being substituted or unsubstituted, and whether substituted or unsubstituted said moieties having less than 21 carbons; each G is independently selected from the group consisting of CO, $SO_2$, SO, PO and $PO_2$; $R^9$ and $R^{10}$ are independently selected from the group consisting of hydrogen and $C_1$-$C_4$ alkyl; $R^{11}$ and $R^{12}$ are independently selected from the group consisting of hydrogen and alkyl, or when taken together may join to form a carbonyl; b=0 or 1; c can=0 or 1, but c must=0 if b=0; y is an integer of from 1 to 6; k is an integer of from 0 to 20; $R^6$ is H, or an alkyl, aryl or heteroaryl moiety; said moieties being substituted or unsubstituted; and X, if present, is a suitable charge balancing counterion.

30. A composition according to claim 1, wherein the bleach catalyst has a chemical structure corresponding to the chemical formula:

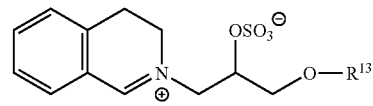

wherein $R^{13}$ is a branched alkyl group containing from 3 to 24 carbons, or a linear alkyl group containing from 1 to 24 carbons.

31. A composition according to claim 1, wherein the bleach catalyst has a chemical structure corresponding to the chemical formula:

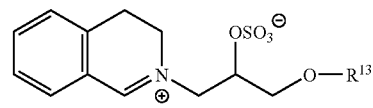

wherein $R^{13}$ is selected from the group consisting of 2-butyloctyl, 2-pentylnonyl, 2-hexyldecyl, iso-tridecyl and iso-pentadecyl.

32. A composition according to claim 1, wherein the composition comprises less than 5%, by weight of the composition, of a source of peroxygen.

33. A composition according to claim 1, wherein the composition comprises from 5% to 10%, by weight of the composition, of a source of carbonate anion.

34. A composition according to claim 1, wherein the composition comprises a dye transfer inhibitor.

35. A composition according to claim 1, wherein the composition comprises:

a) less than 5%, by weight of the composition, of zeolite builder;
b) optionally, less than 5%, by weight of the composition, of phosphate builder; and
c) optionally, less than 5%, by weight of the composition, of silicate salt.

36. A composition according to claim 1, wherein the composition comprises a diacyl and/or a tetraacyl peroxide species.

37. A composition according to claim 1, wherein the composition comprises an oxybenzene sulphonate bleach activator and a source of peroxygen.

38. A composition according to claim 1, wherein the composition comprises a pre-formed peroxyacid.

39. A composition according to claim 1, wherein said lipase variant is a variant of SEQ ID NO: 2 comprising at least one of the mutations Q4V, S58N/A/G/P/T, I 90R or Q249I/L.

* * * * *

SEQUENCE LISTING

<160> NUMBER OF SEQ ID NOS: 16

<210> SEQ ID NO 1
<211> LENGTH: 807
<212> TYPE: DNA
<213> ORGANISM: Thermomyces lanuginosus
<220> FEATURE:
<221> NAME/KEY: CDS
<222> LOCATION: (1)..(807)
<220> FEATURE:
<221> NAME/KEY: mat_peptide

```
<222> LOCATION: (1)..()

<400> SEQUENCE: 1 gag gtc tcg cag gat ctg ttt aac cag ttc aat ctc ttt gca cag tat      48
Glu Val Ser Gln Asp Leu Phe Asn Gln Phe Asn Leu Phe Ala Gln Tyr
1               5                   10                  15 tct gca gcc gca tac tgc gga aaa aac aat gat gcc cca gct ggt aca      96
Ser Ala Ala Ala Tyr Cys Gly Lys Asn Asn Asp Ala Pro Ala Gly Thr
            20                  25                  30 aac att acg tgc acg gga aat gcc tgc ccc gag gta gag aag gcg gat     144
Asn Ile Thr Cys Thr Gly Asn Ala Cys Pro Glu Val Glu Lys Ala Asp
        35                  40                  45 gca acg ttt ctc tac tcg ttt gaa gac tct gga gtg ggc gat gtc acc     192
Ala Thr Phe Leu Tyr Ser Phe Glu Asp Ser Gly Val Gly Asp Val Thr
    50                  55                  60 ggc ttc ctt gct ctc gac aac acg aac aaa ttg atc gtc ctc tct ttc     240
Gly Phe Leu Ala Leu Asp Asn Thr Asn Lys Leu Ile Val Leu Ser Phe
65                  70                  75                  80 cgt ggc tct cgt tcc ata gag aac tgg atc ggg aat ctt aac ttc gac     288
Arg Gly Ser Arg Ser Ile Glu Asn Trp Ile Gly Asn Leu Asn Phe Asp
                85                  90                  95 ttg aaa gaa ata aat gac att tgc tcc ggc tgc agg gga cat gac ggc     336
Leu Lys Glu Ile Asn Asp Ile Cys Ser Gly Cys Arg Gly His Asp Gly
            100                 105                 110 ttc act tcg tcc tgg agg tct gta gcc gat acg tta agg cag aag gtg     384
Phe Thr Ser Ser Trp Arg Ser Val Ala Asp Thr Leu Arg Gln Lys Val
        115                 120                 125 gag gat gct gtg agg gag cat ccc gac tat cgc gtg gtg ttt acc gga     432
Glu Asp Ala Val Arg Glu His Pro Asp Tyr Arg Val Val Phe Thr Gly
    130                 135                 140 cat agc ttg ggt ggt gca ttg gca act gtt gcc gga gca gac ctg cgt     480
His Ser Leu Gly Gly Ala Leu Ala Thr Val Ala Gly Ala Asp Leu Arg
145                 150                 155                 160 gga aat ggg tat gat atc gac gtg ttt tca tat ggc gcc ccc cga gtc     528
Gly Asn Gly Tyr Asp Ile Asp Val Phe Ser Tyr Gly Ala Pro Arg Val
                165                 170                 175 gga aac agg gct ttt gca gaa ttc ctg acc gta cag acc ggc gga aca     576
Gly Asn Arg Ala Phe Ala Glu Phe Leu Thr Val Gln Thr Gly Gly Thr
            180                 185                 190 ctc tac cgc att acc cac acc aat gat att gtc cct aga ctc ccg ccg     624
Leu Tyr Arg Ile Thr His Thr Asn Asp Ile Val Pro Arg Leu Pro Pro
        195                 200                 205 cgc gaa ttc ggt tac agc cat tct agc cca gag tac tgg atc aaa tct     672
Arg Glu Phe Gly Tyr Ser His Ser Ser Pro Glu Tyr Trp Ile Lys Ser
    210                 215                 220 gga acc ctt gtc ccc gtc acc cga aac gat atc gtg aag ata gaa ggc     720
Gly Thr Leu Val Pro Val Thr Arg Asn Asp Ile Val Lys Ile Glu Gly
225                 230                 235                 240 atc gat gcc acc ggc ggc aat aac cag cct aac att ccg gat atc cct     768
Ile Asp Ala Thr Gly Gly Asn Asn Gln Pro Asn Ile Pro Asp Ile Pro
                245                 250                 255 gcg cac cta tgg tac ttc ggg tta att ggg aca tgt ctt                 807
Ala His Leu Trp Tyr Phe Gly Leu Ile Gly Thr Cys Leu
            260                 265

<210> SEQ ID NO 2
<211> LENGTH: 269
<212> TYPE: PRT
<213> ORGANISM: Thermomyces lanuginosus

<400> SEQUENCE: 2
```

```
Glu Val Ser Gln Asp Leu Phe Asn Gln Phe Asn Leu Phe Ala Gln Tyr
1               5                   10                  15

Ser Ala Ala Ala Tyr Cys Gly Lys Asn Asn Asp Ala Pro Ala Gly Thr
            20                  25                  30

Asn Ile Thr Cys Thr Gly Asn Ala Cys Pro Glu Val Glu Lys Ala Asp
        35                  40                  45

Ala Thr Phe Leu Tyr Ser Phe Glu Asp Ser Gly Val Gly Asp Val Thr
    50                  55                  60

Gly Phe Leu Ala Leu Asp Asn Thr Asn Lys Leu Ile Val Leu Ser Phe
65              70                  75                  80

Arg Gly Ser Arg Ser Ile Glu Asn Trp Ile Gly Asn Leu Asn Phe Asp
                85                  90                  95

Leu Lys Glu Ile Asn Asp Ile Cys Ser Gly Cys Arg Gly His Asp Gly
                100                 105                 110

Phe Thr Ser Ser Trp Arg Ser Val Ala Asp Thr Leu Arg Gln Lys Val
            115                 120                 125

Glu Asp Ala Val Arg Glu His Pro Asp Tyr Arg Val Val Phe Thr Gly
130                 135                 140

His Ser Leu Gly Gly Ala Leu Ala Thr Val Ala Gly Ala Asp Leu Arg
145                 150                 155                 160

Gly Asn Gly Tyr Asp Ile Asp Val Phe Ser Tyr Gly Ala Pro Arg Val
                165                 170                 175

Gly Asn Arg Ala Phe Ala Glu Phe Leu Thr Val Gln Thr Gly Gly Thr
            180                 185                 190

Leu Tyr Arg Ile Thr His Thr Asn Asp Ile Val Pro Arg Leu Pro Pro
        195                 200                 205

Arg Glu Phe Gly Tyr Ser His Ser Ser Pro Glu Tyr Trp Ile Lys Ser
    210                 215                 220

Gly Thr Leu Val Pro Val Thr Arg Asn Asp Ile Val Lys Ile Glu Gly
225                 230                 235                 240

Ile Asp Ala Thr Gly Gly Asn Asn Gln Pro Asn Ile Pro Asp Ile Pro
                245                 250                 255

Ala His Leu Trp Tyr Phe Gly Leu Ile Gly Thr Cys Leu
            260                 265

<210> SEQ ID NO 3
<211> LENGTH: 265
<212> TYPE: PRT
<213> ORGANISM: Absidia reflexa

<400> SEQUENCE: 3

Ser Ser Ser Ser Thr Gln Asp Tyr Arg Ile Ala Ser Glu Ala Glu Ile
1               5                   10                  15

Lys Ala His Thr Phe Tyr Thr Ala Leu Ser Ala Asn Ala Tyr Cys Arg
            20                  25                  30

Thr Val Ile Pro Gly Gly Arg Trp Ser Cys Pro His Cys Gly Val Ala
        35                  40                  45

Ser Asn Leu Gln Ile Thr Lys Thr Phe Ser Thr Leu Ile Thr Asp Thr
    50                  55                  60

Asn Val Leu Val Ala Val Gly Glu Lys Glu Lys Thr Ile Tyr Val Val
65              70                  75                  80

Phe Arg Gly Thr Ser Ser Ile Arg Asn Ala Ile Ala Asp Ile Val Phe
            85                  90                  95

Val Pro Val Asn Tyr Pro Pro Val Asn Gly Ala Lys Val His Lys Gly
```

```
                100                 105                 110
Phe Leu Asp Ser Tyr Asn Glu Val Gln Asp Lys Leu Val Ala Glu Val
            115                 120                 125

Lys Ala Gln Leu Asp Arg His Pro Gly Tyr Lys Ile Val Thr Gly
        130                 135                 140

His Ser Leu Gly Gly Ala Thr Ala Val Leu Ser Ala Leu Asp Leu Tyr
145                 150                 155                 160

His His Gly His Ala Asn Ile Glu Ile Tyr Thr Gln Gly Gln Pro Arg
                165                 170                 175

Ile Gly Thr Pro Ala Phe Ala Asn Tyr Val Ile Gly Thr Lys Ile Pro
            180                 185                 190

Tyr Gln Arg Leu Val His Glu Arg Asp Ile Val Pro His Leu Pro Pro
        195                 200                 205

Gly Ala Phe Gly Phe Leu His Ala Gly Glu Glu Phe Trp Ile Met Lys
    210                 215                 220

Asp Ser Ser Leu Arg Val Cys Pro Asn Gly Ile Glu Thr Asp Asn Cys
225                 230                 235                 240

Ser Asn Ser Ile Val Pro Phe Thr Ser Val Ile Asp His Leu Ser Tyr
                245                 250                 255

Leu Asp Met Asn Thr Gly Leu Cys Leu
                260                 265

<210> SEQ ID NO 4
<211> LENGTH: 264
<212> TYPE: PRT
<213> ORGANISM: Absidia corymbifera

<400> SEQUENCE: 4

Ser Ser Ser Thr Gln Asp Tyr Arg Ile Ala Ser Glu Ala Glu Ile Lys
1               5                   10                  15

Ala His Thr Phe Tyr Thr Ala Leu Ser Ala Asn Ala Tyr Cys Arg Thr
            20                  25                  30

Val Ile Pro Gly Gly Gln Trp Ser Cys Pro His Cys Asp Val Ala Pro
        35                  40                  45

Asn Leu Asn Ile Thr Lys Thr Phe Thr Thr Leu Ile Thr Asp Thr Asn
    50                  55                  60

Val Leu Val Ala Val Gly Glu Asn Glu Lys Thr Ile Tyr Val Val Phe
65                  70                  75                  80

Arg Gly Thr Ser Ser Ile Arg Asn Ala Ile Ala Asp Ile Val Phe Val
                85                  90                  95

Pro Val Asn Tyr Pro Pro Val Asn Gly Ala Lys Val His Lys Gly Phe
            100                 105                 110

Leu Asp Ser Tyr Asn Glu Val Gln Asp Lys Leu Val Ala Glu Val Lys
        115                 120                 125

Ala Gln Leu Asp Arg His Pro Gly Tyr Lys Ile Val Thr Gly His
    130                 135                 140

Ser Leu Gly Gly Ala Thr Ala Val Leu Ser Ala Leu Asp Leu Tyr His
145                 150                 155                 160

His Gly His Asp Asn Ile Glu Ile Tyr Thr Gln Gly Gln Pro Arg Ile
                165                 170                 175

Gly Thr Pro Glu Phe Ala Asn Tyr Val Ile Gly Thr Lys Ile Pro Tyr
            180                 185                 190

Gln Arg Leu Val Asn Glu Arg Asp Ile Val Pro His Leu Pro Pro Gly
        195                 200                 205
```

```
Ala Phe Gly Phe Leu His Ala Gly Glu Glu Phe Trp Ile Met Lys Asp
    210                 215                 220

Ser Ser Leu Arg Val Cys Pro Asn Gly Ile Glu Thr Asp Asn Cys Ser
225                 230                 235                 240

Asn Ser Ile Val Pro Phe Thr Ser Val Ile Asp His Leu Ser Tyr Leu
                245                 250                 255

Asp Met Asn Thr Gly Leu Cys Leu
            260

<210> SEQ ID NO 5
<211> LENGTH: 269
<212> TYPE: PRT
<213> ORGANISM: Rhizomucor miehei

<400> SEQUENCE: 5

Ser Ile Asp Gly Gly Ile Arg Ala Ala Thr Ser Gln Glu Ile Asn Glu
  1               5                  10                  15

Leu Thr Tyr Tyr Thr Thr Leu Ser Ala Asn Ser Tyr Cys Arg Thr Val
                 20                  25                  30

Ile Pro Gly Ala Thr Trp Asp Cys Ile His Cys Asp Ala Thr Glu Asp
             35                  40                  45

Leu Lys Ile Ile Lys Thr Trp Ser Thr Leu Ile Tyr Asp Thr Asn Ala
 50                  55                  60

Met Val Ala Arg Gly Asp Ser Glu Lys Thr Ile Tyr Ile Val Phe Arg
 65                  70                  75                  80

Gly Ser Ser Ser Ile Arg Asn Trp Ile Ala Asp Leu Thr Phe Val Pro
                 85                  90                  95

Val Ser Tyr Pro Pro Val Ser Gly Thr Lys Val His Lys Gly Phe Leu
                100                 105                 110

Asp Ser Tyr Gly Glu Val Gln Asn Glu Leu Val Ala Thr Val Leu Asp
            115                 120                 125

Gln Phe Lys Gln Tyr Pro Ser Tyr Lys Val Ala Val Thr Gly His Ser
130                 135                 140

Leu Gly Gly Ala Thr Ala Leu Leu Cys Ala Leu Asp Leu Tyr Gln Arg
145                 150                 155                 160

Glu Glu Gly Leu Ser Ser Ser Asn Leu Phe Leu Tyr Thr Gln Gly Gln
                165                 170                 175

Pro Arg Val Gly Asp Pro Ala Phe Ala Asn Tyr Val Val Ser Thr Gly
            180                 185                 190

Ile Pro Tyr Arg Arg Thr Val Asn Glu Arg Asp Ile Val Pro His Leu
        195                 200                 205

Pro Pro Ala Ala Phe Gly Phe Leu His Ala Gly Glu Glu Tyr Trp Ile
    210                 215                 220

Thr Asp Asn Ser Pro Glu Thr Val Gln Val Cys Thr Ser Asp Leu Glu
225                 230                 235                 240

Thr Ser Asp Cys Ser Asn Ser Ile Val Pro Phe Thr Ser Val Leu Asp
                245                 250                 255

His Leu Ser Tyr Phe Gly Ile Asn Thr Gly Leu Cys Thr
            260                 265

<210> SEQ ID NO 6
<211> LENGTH: 271
<212> TYPE: PRT
<213> ORGANISM: Rhizopus oryzae

<400> SEQUENCE: 6
```

```
Ser Ala Ser Asp Gly Lys Val Val Ala Thr Thr Ala Gln Ile
1               5                   10                  15

Gln Glu Phe Thr Lys Tyr Ala Gly Ile Ala Ala Thr Ala Tyr Cys Arg
            20                  25                  30

Ser Val Val Pro Gly Asn Lys Trp Asp Cys Val Gln Cys Gln Lys Trp
                35                  40                  45

Val Pro Asp Gly Lys Ile Ile Thr Thr Phe Thr Ser Leu Leu Ser Asp
    50                  55                  60

Thr Asn Gly Tyr Val Leu Arg Ser Asp Lys Gln Lys Thr Ile Tyr Leu
65                  70                  75                  80

Val Phe Arg Gly Thr Asn Ser Phe Arg Ser Ala Ile Thr Asp Ile Val
                85                  90                  95

Phe Asn Phe Ser Asp Tyr Lys Pro Val Lys Gly Ala Lys Val His Ala
                100                 105                 110

Gly Phe Leu Ser Ser Tyr Glu Gln Val Val Asn Asp Tyr Phe Pro Val
            115                 120                 125

Val Gln Glu Gln Leu Thr Ala His Pro Thr Tyr Lys Val Ile Val Thr
130                 135                 140

Gly His Ser Leu Gly Gly Ala Gln Ala Leu Leu Ala Gly Met Asp Leu
145                 150                 155                 160

Tyr Gln Arg Glu Pro Arg Leu Ser Pro Lys Asn Leu Ser Ile Phe Thr
                165                 170                 175

Val Gly Gly Pro Arg Val Gly Asn Pro Thr Phe Ala Tyr Tyr Val Glu
            180                 185                 190

Ser Thr Gly Ile Pro Phe Gln Arg Thr Val His Lys Arg Asp Ile Val
            195                 200                 205

Pro His Val Pro Pro Gln Ser Phe Gly Phe Leu His Pro Gly Val Glu
    210                 215                 220

Ser Trp Ile Lys Ser Gly Thr Ser Asn Val Gln Ile Cys Thr Ser Glu
225                 230                 235                 240

Ile Glu Thr Lys Asp Cys Ser Asn Ser Ile Val Pro Phe Thr Ser Ile
                245                 250                 255

Leu Asp His Leu Ser Tyr Phe Asp Ile Asn Glu Gly Ser Cys Leu
                260                 265                 270

<210> SEQ ID NO 7
<211> LENGTH: 267
<212> TYPE: PRT
<213> ORGANISM: Aspergillus niger

<400> SEQUENCE: 7

Thr Ala Gly His Ala Leu Ala Ala Ser Thr Gln Gly Ile Ser Glu Asp
1               5                   10                  15

Leu Tyr Ser Arg Leu Val Glu Met Ala Thr Ile Ser Gln Ala Ala Tyr
            20                  25                  30

Ala Asp Leu Cys Asn Ile Pro Ser Thr Ile Ile Lys Gly Glu Lys Ile
        35                  40                  45

Tyr Asn Ser Gln Thr Asp Ile Asn Gly Trp Ile Leu Arg Asp Asp Ser
    50                  55                  60

Ser Lys Glu Ile Ile Thr Val Phe Arg Gly Thr Gly Ser Asp Thr Asn
65                  70                  75                  80

Leu Gln Leu Asp Thr Asn Tyr Thr Leu Thr Pro Phe Asp Thr Leu Pro
                85                  90                  95

Gln Cys Asn Gly Cys Glu Val His Gly Gly Tyr Tyr Ile Gly Trp Val
            100                 105                 110
```

```
Ser Val Gln Asp Gln Val Glu Ser Leu Val Lys Gln Val Ser Gln
            115                 120                 125
Tyr Pro Asp Tyr Ala Leu Thr Val Thr Gly His Ser Leu Gly Ala Ser
    130                 135                 140
Leu Ala Ala Leu Thr Ala Ala Gln Leu Ser Ala Thr Tyr Asp Asn Ile
145                 150                 155                 160
Arg Leu Tyr Thr Phe Gly Glu Pro Arg Ser Gly Asn Gln Ala Phe Ala
                165                 170                 175
Ser Tyr Met Asn Asp Ala Phe Gln Ala Ser Ser Pro Asp Thr Thr Gln
            180                 185                 190
Tyr Phe Arg Val Thr His Ala Asn Asp Gly Ile Pro Asn Leu Pro Pro
        195                 200                 205
Val Glu Gln Gly Tyr Ala His Gly Gly Val Glu Tyr Trp Ser Val Asp
    210                 215                 220
Pro Tyr Ser Ala Gln Asn Thr Phe Val Cys Thr Gly Asp Glu Val Gln
225                 230                 235                 240
Cys Cys Glu Ala Gln Gly Gly Gln Gly Val Asn Asn Ala His Thr Thr
                245                 250                 255
Tyr Phe Gly Met Thr Ser Gly Ala Cys Thr Trp
            260                 265

<210> SEQ ID NO 8
<211> LENGTH: 266
<212> TYPE: PRT
<213> ORGANISM: Aspergillus tubingensis

<400> SEQUENCE: 8

Thr Ala Gly His Ala Leu Ala Ala Ser Thr Gln Gly Ile Ser Glu Asp
1               5                   10                  15
Leu Tyr Ser Arg Leu Val Glu Met Ala Thr Ile Ser Gln Ala Ala Tyr
            20                  25                  30
Ala Asp Leu Cys Asn Ile Pro Ser Thr Ile Ile Lys Gly Glu Lys Ile
        35                  40                  45
Tyr Asn Ser Gln Thr Asp Ile Asn Gly Trp Ile Leu Arg Asp Asp Ser
    50                  55                  60
Ser Lys Glu Ile Ile Thr Val Phe Arg Gly Thr Gly Ser Asp Thr Asn
65                  70                  75                  80
Leu Gln Leu Asp Thr Asn Tyr Thr Leu Thr Pro Phe Asp Thr Leu Pro
                85                  90                  95
Gln Cys Asn Ser Cys Glu Val His Gly Gly Tyr Tyr Ile Gly Trp Ile
            100                 105                 110
Ser Val Gln Asp Gln Val Glu Ser Leu Val Gln Gln Val Ser Gln
            115                 120                 125
Phe Pro Asp Tyr Ala Leu Thr Val Thr Gly His Ser Leu Gly Ala Ser
    130                 135                 140
Leu Ala Ala Leu Thr Ala Ala Gln Leu Ser Ala Thr Tyr Asp Asn Ile
145                 150                 155                 160
Arg Leu Tyr Thr Phe Gly Glu Pro Arg Ser Asn Gln Ala Phe Ala Ser
                165                 170                 175
Tyr Met Asn Asp Ala Phe Gln Ala Ser Ser Pro Asp Thr Thr Gln Tyr
            180                 185                 190
Phe Arg Val Thr His Ala Asn Asp Gly Ile Pro Asn Leu Pro Pro Ala
        195                 200                 205
Asp Glu Gly Tyr Ala His Gly Val Val Glu Tyr Trp Ser Val Asp Pro
```

-continued

```
                210                 215                 220
Tyr Ser Ala Gln Asn Thr Phe Val Cys Thr Gly Asp Glu Val Gln Cys
225                 230                 235                 240

Cys Glu Ala Gln Gly Gly Gln Gly Val Asn Asn Ala His Thr Thr Tyr
                245                 250                 255

Phe Gly Met Thr Ser Gly His Cys Thr Trp
                260                 265

<210> SEQ ID NO 9
<211> LENGTH: 276
<212> TYPE: PRT
<213> ORGANISM: Fusarium oxysporum

<400> SEQUENCE: 9

Ala Val Gly Val Thr Thr Thr Asp Phe Ser Asn Phe Lys Phe Tyr Ile
1               5                   10                  15

Gln His Gly Ala Ala Ala Tyr Cys Asn Ser Glu Ala Ala Gly Ser
                20                  25                  30

Lys Ile Thr Cys Ser Asn Asn Gly Cys Pro Thr Val Gln Gly Asn Gly
                35                  40                  45

Ala Thr Ile Val Thr Ser Phe Val Gly Ser Lys Thr Gly Ile Gly Gly
50                  55                  60

Tyr Val Ala Thr Asp Ser Ala Arg Lys Glu Ile Val Ser Phe Arg
65                  70                  75                  80

Gly Ser Ile Asn Ile Arg Asn Trp Leu Thr Asn Leu Asp Phe Gly Gln
                85                  90                  95

Glu Asp Cys Ser Leu Val Ser Gly Cys Gly Val His Ser Gly Phe Gln
                100                 105                 110

Arg Ala Trp Asn Glu Ile Ser Ser Gln Ala Thr Ala Ala Val Ala Ser
                115                 120                 125

Ala Arg Lys Ala Asn Pro Ser Phe Asn Val Ile Ser Thr Gly His Ser
130                 135                 140

Leu Gly Gly Ala Val Ala Val Leu Ala Ala Ala Asn Leu Arg Val Gly
145                 150                 155                 160

Gly Thr Pro Val Asp Ile Tyr Thr Tyr Gly Ser Pro Arg Val Gly Asn
                165                 170                 175

Ala Gln Leu Ser Ala Phe Val Ser Asn Gln Ala Gly Gly Glu Tyr Arg
                180                 185                 190

Val Thr His Ala Asp Asp Pro Val Pro Arg Leu Pro Pro Leu Ile Phe
                195                 200                 205

Gly Tyr Arg His Thr Thr Pro Glu Phe Trp Leu Ser Gly Gly Gly Gly
210                 215                 220

Asp Lys Val Asp Tyr Thr Ile Ser Asp Val Lys Val Cys Glu Gly Ala
225                 230                 235                 240

Ala Asn Leu Gly Cys Asn Gly Gly Thr Leu Gly Leu Asp Ile Ala Ala
                245                 250                 255

His Leu His Tyr Phe Gln Ala Thr Asp Ala Cys Asn Ala Gly Gly Phe
                260                 265                 270

Ser Trp Arg Arg
        275

<210> SEQ ID NO 10
<211> LENGTH: 273
<212> TYPE: PRT
<213> ORGANISM: Fusarium heterosporum
```

<400> SEQUENCE: 10

```
Thr Val Thr Thr Gln Asp Leu Ser Asn Phe Arg Phe Tyr Leu Gln His
1               5                   10                  15

Ala Asp Ala Ala Tyr Cys Asn Phe Asn Thr Ala Val Gly Lys Pro Val
            20                  25                  30

His Cys Ser Ala Gly Asn Cys Pro Asp Ile Glu Lys Asp Ala Ala Ile
        35                  40                  45

Val Val Gly Ser Val Val Gly Thr Lys Thr Gly Ile Gly Ala Tyr Val
    50                  55                  60

Ala Thr Asp Asn Ala Arg Lys Glu Ile Val Val Ser Val Arg Gly Ser
65                  70                  75                  80

Ile Asn Val Arg Asn Trp Ile Thr Asn Phe Asn Phe Gly Gln Lys Thr
                85                  90                  95

Cys Asp Leu Val Ala Gly Cys Gly Val His Thr Gly Phe Leu Asp Ala
            100                 105                 110

Trp Glu Glu Val Ala Ala Asn Val Lys Ala Ala Val Ser Ala Ala Lys
        115                 120                 125

Thr Ala Asn Pro Thr Phe Lys Phe Val Val Thr Gly His Ser Leu Gly
    130                 135                 140

Gly Ala Val Ala Thr Ile Ala Ala Ala Tyr Leu Arg Lys Asp Gly Phe
145                 150                 155                 160

Pro Phe Asp Leu Tyr Thr Tyr Gly Ser Pro Arg Val Gly Asn Asp Phe
                165                 170                 175

Phe Ala Asn Phe Val Thr Gln Gln Thr Gly Ala Glu Tyr Arg Val Thr
            180                 185                 190

His Gly Asp Asp Pro Val Pro Arg Leu Pro Pro Ile Val Phe Gly Tyr
        195                 200                 205

Arg His Thr Ser Pro Glu Tyr Trp Leu Asn Gly Gly Pro Leu Asp Lys
    210                 215                 220

Asp Tyr Thr Val Thr Glu Ile Lys Val Cys Glu Gly Ile Ala Asn Val
225                 230                 235                 240

Met Cys Asn Gly Gly Thr Ile Gly Leu Asp Ile Leu Ala His Ile Thr
                245                 250                 255

Tyr Phe Gln Ser Met Ala Thr Cys Ala Pro Ile Ala Ile Pro Trp Lys
            260                 265                 270

Arg
```

<210> SEQ ID NO 11
<211> LENGTH: 278
<212> TYPE: PRT
<213> ORGANISM: Aspergillus oryzae

<400> SEQUENCE: 11

```
Asp Ile Pro Thr Thr Gln Leu Glu Asp Phe Lys Phe Trp Val Gln Tyr
1               5                   10                  15

Ala Ala Ala Thr Tyr Cys Pro Asn Asn Tyr Val Ala Lys Asp Gly Glu
            20                  25                  30

Lys Leu Asn Cys Ser Val Gly Asn Cys Pro Asp Val Glu Ala Ala Gly
        35                  40                  45

Ser Thr Val Lys Leu Ser Phe Ser Asp Asp Thr Ile Thr Asp Thr Ala
    50                  55                  60

Gly Phe Val Ala Val Asp Asn Thr Asn Lys Ala Ile Val Val Ala Phe
65                  70                  75                  80

Arg Gly Ser Tyr Ser Ile Arg Asn Trp Val Thr Asp Ala Thr Phe Pro
```

-continued

```
                85                  90                  95
Gln Thr Asp Pro Gly Leu Cys Asp Gly Cys Lys Ala Glu Leu Gly Phe
            100                 105                 110

Trp Thr Ala Trp Lys Val Val Arg Asp Arg Ile Ile Lys Thr Leu Asp
        115                 120                 125

Glu Leu Lys Pro Glu His Ser Asp Tyr Lys Ile Val Val Gly His
    130                 135                 140

Ser Leu Gly Ala Ala Ile Ala Ser Leu Ala Ala Ala Asp Leu Arg Thr
145                 150                 155                 160

Lys Asn Tyr Asp Ala Ile Leu Tyr Ala Tyr Ala Ala Pro Arg Val Ala
                165                 170                 175

Asn Lys Pro Leu Ala Glu Phe Ile Thr Asn Gln Gly Asn Asn Tyr Arg
            180                 185                 190

Phe Thr His Asn Asp Asp Pro Val Pro Lys Leu Pro Leu Leu Thr Met
        195                 200                 205

Gly Tyr Val His Ile Ser Pro Glu Tyr Tyr Ile Thr Ala Pro Asp Asn
    210                 215                 220

Thr Thr Val Thr Asp Asn Gln Val Thr Val Leu Asp Gly Tyr Val Asn
225                 230                 235                 240

Phe Lys Gly Asn Thr Gly Thr Ser Gly Gly Leu Pro Asp Leu Leu Ala
                245                 250                 255

Phe His Ser His Val Trp Tyr Phe Ile His Ala Asp Ala Cys Lys Gly
            260                 265                 270

Pro Gly Leu Pro Leu Arg
        275

<210> SEQ ID NO 12
<211> LENGTH: 278
<212> TYPE: PRT
<213> ORGANISM: Penicillium camemberti

<400> SEQUENCE: 12

Asp Val Ser Thr Ser Glu Leu Asp Gln Phe Glu Phe Trp Val Gln Tyr
1               5                   10                  15

Ala Ala Ala Ser Tyr Tyr Glu Ala Asp Tyr Thr Ala Gln Val Gly Asp
                20                  25                  30

Lys Leu Ser Cys Ser Lys Gly Asn Cys Pro Glu Val Glu Ala Thr Gly
            35                  40                  45

Ala Thr Val Ser Tyr Asp Phe Ser Asp Ser Thr Ile Thr Asp Thr Ala
        50                  55                  60

Gly Tyr Ile Ala Val Asp His Thr Asn Ser Ala Val Val Leu Ala Phe
65                  70                  75                  80

Arg Gly Ser Tyr Ser Val Arg Asn Trp Val Ala Asp Ala Thr Phe Val
                85                  90                  95

His Thr Asn Pro Gly Leu Cys Asp Gly Cys Leu Ala Glu Leu Gly Phe
            100                 105                 110

Trp Ser Ser Trp Lys Leu Val Arg Asp Asp Ile Ile Lys Glu Leu Lys
        115                 120                 125

Glu Val Val Ala Gln Asn Pro Asn Tyr Glu Leu Val Val Gly His
    130                 135                 140

Ser Leu Gly Ala Ala Val Ala Thr Leu Ala Ala Thr Asp Leu Arg Gly
145                 150                 155                 160

Lys Gly Tyr Pro Ser Ala Lys Leu Tyr Ala Tyr Ala Ser Pro Arg Val
                165                 170                 175
```

```
Gly Asn Ala Ala Leu Ala Lys Tyr Ile Thr Ala Gln Gly Asn Asn Phe
                180                 185                 190

Arg Phe Thr His Thr Asn Asp Pro Val Pro Lys Leu Pro Leu Leu Ser
            195                 200                 205

Met Gly Tyr Val His Val Ser Pro Glu Tyr Trp Ile Thr Ser Pro Asn
    210                 215                 220

Asn Ala Thr Val Ser Thr Ser Asp Ile Lys Val Ile Asp Gly Asp Val
225                 230                 235                 240

Ser Phe Asp Gly Asn Thr Gly Thr Gly Leu Pro Leu Leu Thr Asp Phe
                245                 250                 255

Glu Ala His Ile Trp Tyr Phe Val Gln Val Asp Ala Gly Lys Gly Pro
            260                 265                 270

Gly Leu Pro Phe Lys Arg
            275

<210> SEQ ID NO 13
<211> LENGTH: 270
<212> TYPE: PRT
<213> ORGANISM: Aspergillus foetidus

<400> SEQUENCE: 13

Ser Val Ser Thr Ser Thr Leu Asp Glu Leu Gln Leu Phe Ala Gln Trp
1               5                   10                  15

Ser Ala Ala Ala Tyr Cys Ser Asn Asn Ile Asp Ser Lys Asp Ser Asn
                20                  25                  30

Leu Thr Cys Thr Ala Asn Ala Cys Pro Ser Val Glu Glu Ala Ser Thr
            35                  40                  45

Thr Met Leu Leu Glu Phe Asp Leu Thr Asn Asp Phe Gly Gly Thr Ala
    50                  55                  60

Gly Phe Leu Ala Ala Asp Asn Thr Asn Lys Arg Leu Val Val Ala Phe
65                  70                  75                  80

Arg Gly Ser Ser Thr Ile Glu Asn Trp Ile Ala Asn Leu Asp Phe Ile
                85                  90                  95

Leu Glu Asp Asn Asp Asp Leu Cys Thr Gly Cys Lys Val His Thr Gly
                100                 105                 110

Phe Trp Lys Ala Trp Glu Ser Ala Ala Asp Glu Leu Thr Ser Lys Ile
            115                 120                 125

Lys Ser Ala Met Ser Thr Tyr Ser Gly Tyr Thr Leu Tyr Phe Thr Gly
    130                 135                 140

His Ser Leu Gly Gly Ala Leu Ala Thr Leu Gly Ala Thr Val Leu Arg
145                 150                 155                 160

Asn Asp Gly Tyr Ser Val Glu Leu Tyr Thr Tyr Gly Cys Pro Arg Ile
                165                 170                 175

Gly Asn Tyr Ala Leu Ala Glu His Ile Thr Ser Gln Gly Ser Gly Ala
            180                 185                 190

Asn Phe Arg Val Thr His Leu Asn Asp Ile Val Pro Arg Val Pro Pro
        195                 200                 205

Met Asp Phe Gly Phe Ser Gln Pro Ser Pro Glu Tyr Trp Ile Thr Ser
    210                 215                 220

Gly Asn Gly Ala Ser Val Thr Ala Ser Asp Ile Glu Val Ile Glu Gly
225                 230                 235                 240

Ile Asn Ser Thr Ala Gly Asn Ala Gly Glu Ala Thr Val Ser Val Leu
                245                 250                 255

Ala His Leu Trp Tyr Phe Phe Ala Ile Ser Glu Cys Leu Leu
            260                 265                 270
```

```
<210> SEQ ID NO 14
<211> LENGTH: 270
<212> TYPE: PRT
<213> ORGANISM: Aspergillus niger

<400> SEQUENCE: 14

Ser Val Ser Thr Ser Thr Leu Asp Glu Leu Gln Leu Phe Ser Gln Trp
1               5                   10                  15

Ser Ala Ala Tyr Cys Ser Asn Asn Ile Asp Ser Asp Ser Asn
            20                  25                  30

Val Thr Cys Thr Ala Asp Ala Cys Pro Ser Val Glu Glu Ala Ser Thr
            35                  40                  45

Lys Met Leu Leu Glu Phe Asp Leu Thr Asn Asn Phe Gly Gly Thr Ala
        50                  55                  60

Gly Phe Leu Ala Ala Asp Asn Thr Asn Lys Arg Leu Val Val Ala Phe
65                  70                  75                  80

Arg Gly Ser Ser Thr Ile Lys Asn Trp Ile Ala Asp Leu Asp Phe Ile
                85                  90                  95

Leu Gln Asp Asn Asp Asp Leu Cys Thr Gly Cys Lys Val His Thr Gly
            100                 105                 110

Phe Trp Lys Ala Trp Glu Ala Ala Asp Asn Leu Thr Ser Lys Ile
            115                 120                 125

Lys Ser Ala Met Ser Thr Tyr Ser Gly Tyr Thr Leu Tyr Phe Thr Gly
        130                 135                 140

His Ser Leu Gly Gly Ala Leu Ala Thr Leu Gly Ala Thr Val Leu Arg
145                 150                 155                 160

Asn Asp Gly Tyr Ser Val Glu Leu Tyr Thr Tyr Gly Cys Pro Arg Val
                165                 170                 175

Gly Asn Tyr Ala Leu Ala Glu His Ile Thr Ser Gln Gly Ser Gly Ala
            180                 185                 190

Asn Phe Pro Val Thr His Leu Asn Asp Ile Val Pro Arg Val Pro Pro
        195                 200                 205

Met Asp Phe Gly Phe Ser Gln Pro Ser Pro Glu Tyr Trp Ile Thr Ser
210                 215                 220

Gly Thr Gly Ala Ser Val Thr Ala Ser Asp Ile Glu Leu Ile Glu Gly
225                 230                 235                 240

Ile Asn Ser Thr Ala Gly Asn Ala Gly Glu Ala Thr Val Asp Val Leu
                245                 250                 255

Ala His Leu Trp Tyr Phe Phe Ala Ile Ser Glu Cys Leu Leu
            260                 265                 270

<210> SEQ ID NO 15
<211> LENGTH: 269
<212> TYPE: PRT
<213> ORGANISM: Aspergillus oryzae

<400> SEQUENCE: 15

Asp Val Ser Ser Ser Leu Leu Asn Asn Leu Asp Leu Phe Ala Gln Tyr
1               5                   10                  15

Ser Ala Ala Tyr Cys Asp Glu Asn Leu Asn Ser Thr Gly Thr Lys
            20                  25                  30

Leu Thr Cys Ser Val Gly Asn Cys Pro Leu Val Glu Ala Ala Ser Thr
            35                  40                  45

Gln Ser Leu Asp Glu Phe Asn Glu Ser Ser Ser Tyr Gly Asn Pro Ala
        50                  55                  60
```

Gly Tyr Leu Ala Ala Asp Glu Thr Asn Lys Leu Leu Val Leu Ser Phe
65                  70                  75                  80

Arg Gly Ser Ala Asp Leu Ala Asn Trp Val Ala Asn Leu Asn Phe Gly
                85                  90                  95

Leu Glu Asp Ala Ser Asp Leu Cys Ser Gly Cys Glu Val His Ser Gly
            100                 105                 110

Phe Trp Lys Ala Trp Ser Glu Ile Ala Asp Thr Ile Thr Ser Lys Val
        115                 120                 125

Glu Ser Ala Leu Ser Asp His Ser Asp Tyr Ser Leu Val Leu Thr Gly
130                 135                 140

His Ser Tyr Gly Ala Ala Leu Ala Ala Leu Ala Ala Thr Ala Leu Arg
145                 150                 155                 160

Asn Ser Gly His Ser Val Glu Leu Tyr Asn Tyr Gly Gln Pro Arg Leu
                165                 170                 175

Gly Asn Glu Ala Leu Ala Thr Tyr Ile Thr Asp Gln Asn Lys Gly Gly
            180                 185                 190

Asn Tyr Arg Val Thr His Thr Asn Asp Ile Val Pro Lys Leu Pro Pro
        195                 200                 205

Thr Leu Leu Gly Tyr His His Phe Ser Pro Glu Tyr Tyr Ile Ser Ser
210                 215                 220

Ala Asp Glu Ala Thr Val Thr Thr Thr Asp Val Thr Glu Val Thr Gly
225                 230                 235                 240

Ile Asp Ala Thr Gly Gly Asn Asp Gly Thr Asp Gly Thr Ser Ile Asp
                245                 250                 255

Ala His Arg Trp Tyr Phe Ile Tyr Ile Ser Glu Cys Ser
            260                 265

<210> SEQ ID NO 16
<211> LENGTH: 251
<212> TYPE: PRT
<213> ORGANISM: Landerina penisapora

<400> SEQUENCE: 16

Pro Gln Asp Ala Tyr Thr Ala Ser His Ala Asp Leu Val Lys Tyr Ala
1               5                   10                  15

Thr Tyr Ala Gly Leu Ala Tyr Gln Thr Thr Asp Ala Trp Pro Ala Ser
                20                  25                  30

Arg Thr Val Pro Lys Asp Thr Thr Leu Ile Ser Ser Phe Asp His Thr
            35                  40                  45

Leu Lys Gly Ser Ser Gly Tyr Ile Ala Phe Asn Glu Pro Cys Lys Glu
        50                  55                  60

Ile Ile Val Ala Tyr Arg Gly Thr Asp Ser Leu Ile Asp Trp Leu Thr
65                  70                  75                  80

Asn Leu Asn Phe Asp Lys Thr Ala Trp Pro Ala Asn Ile Ser Asn Ser
                85                  90                  95

Leu Val His Glu Gly Phe Leu Asn Ala Tyr Leu Val Ser Met Gln Gln
            100                 105                 110

Val Gln Glu Ala Val Asp Ser Leu Leu Ala Lys Cys Pro Asp Ala Thr
        115                 120                 125

Ile Ser Phe Thr Gly His Ser Leu Gly Gly Ala Leu Ala Cys Ile Ser
130                 135                 140

Met Val Asp Thr Ala Gln Arg His Arg Gly Ile Lys Met Gln Met Phe
145                 150                 155                 160

Thr Tyr Gly Gln Pro Arg Thr Gly Asn Gln Ala Phe Ala Glu Tyr Val

-continued

```
                165                 170                 175
Glu Asn Leu Gly His Pro Val Phe Arg Val Val Tyr Arg His Asp Ile
            180                 185                 190

Val Pro Arg Met Pro Pro Met Asp Leu Gly Phe Gln His His Gly Gln
        195                 200                 205

Glu Val Trp Tyr Glu Gly Asp Glu Asn Ile Lys Phe Cys Lys Gly Glu
    210                 215                 220

Gly Glu Asn Leu Thr Cys Glu Leu Gly Val Pro Phe Ser Glu Leu Asn
225                 230                 235                 240

Ala Lys Asp His Ser Glu Tyr Pro Gly Met His
            245                 250
```